United States Patent [19]
Lalouel et al.

[11] Patent Number: 5,763,168
[45] Date of Patent: Jun. 9, 1998

[54] METHOD TO DETERMINE PREDISPOSITION TO HYPERTENSION

[75] Inventors: Jean-Marc Lalouel, Salt Lake City, Utah; Xavier Jeunemaitre, Paris, France; Richard P. Lifton, Guilford, Conn.; Florent Soubrier, Paris, France; Youri Kotelevtsev, Edinburgh, United Kingdom; Pierre Corvol, Paris, France

[73] Assignees: University of Utah Research Foundation, Salt Lake City, Utah; INSERM, Paris, France

[21] Appl. No.: 319,545

[22] Filed: Oct. 7, 1994

Related U.S. Application Data

[63] Continuation-in-part of Ser. No. 952,442, Sep. 30, 1992, Pat. No. 5,374,525.

[51] Int. Cl.[6] .............................. C12Q 1/68; C07H 21/04
[52] U.S. Cl. ............................ 435/6; 536/23.5; 536/24.31; 935/8; 935/9; 935/77; 935/78
[58] Field of Search ................... 435/6; 536/23.5, 536/24.31; 935/77, 78, 8, 9

[56] References Cited

PUBLICATIONS

Caulfield et al, The New England Journal of Medicine (1994) 330: 1629–1633.
Morgan et al, Human Genetics (1996) 98: 194–198.
Kageyama, Ryoichiro et al. (1984). "Primary Structure of Human Preangiotensinogen Deduced from the Cloned cDNA Sequence," Biochem. 23:3603–3609.
Kunapuli, S.P. and Kumar, A. (1986). "Difference in the Nucleotide Sequence of Human Angiotensinogen cDNA," Nucl. Acids Res. 14:7509.
Gaillard, I. et al. (1989). "Structure of Human Angiotensinogen Gene," DNA 8:87–99.
Fukamizu, A. et al. (1990). "Structure and Expression of the Human Angiotensinogen Gene," J. Biol. Chem. 265:7576–7582.

Soubrier, F. et al. (1990). "Similar Frequencies of Renin Gene Restriction Fragment Length Polymorphisms in Hypertensive and Normotensive Subjects," Hypertension 16:712–717.
Kotelevtsev, Y.V. et al. (1991). "Dinucleotide Repeat Polymorphism in the Human Angiotensinogen Gene," Nucl. Acids Res. 19:6978.
Jeunemaitre, X. et al. (1992). "Absence of Linkage Between the Angiotensin Converting Enzyme Locus and Human Essential Hypertension," Nature Genetics 1:72–75.
Jeunemaitre, X. et al. (1992). "Sib Pair Linkage Analysis of Renin Gene Haplotypes in Human Essential Hypertension," Human Genetics 88:301–306.
Jeunemaitre, X. et al. (1992). "Molecular Basis of Human Hypertension: Role of Angiotensinogen," Cell 71:169–180.
Jeunemaitre, X. et al. (1993). "M235T variant of the human angiotensinogen gene in unselected hypertensive patients," J. Hypertension 11(supp. 5):S80–S81.
Bennett, C.L. et al. (1993). "Cross–sectional Analysis of Met[235]→ Thr Variant of Angiotensinogen Gene in Severe, Familial Hypertension," Biochem. Biophys. Res. Commun. 197:833–839.
Hata, A. et al. (1994). "Angiotensinogen as a Risk Factor for Essential Hypertension in Japan," J. Clin. Invest. 93:1285–1287.
Grim et al. (1994). "The Angiotensinogen Gene MT235 is not Associated with Blood Pressure in Blacks on Dominica," Abstract 49 from an unknown source.

(List continued on next page.)

*Primary Examiner*—Carla J. Myers
*Attorney, Agent, or Firm*—Venable, Baetjer, Howard & Civiletti, LLP

[57] ABSTRACT

The association of the molecular variant G-6A of the angiotensinogen gene with human hypertension is disclosed. The determination of this association enables the screening of persons to identify those who have a predisposition to high blood presure.

9 Claims, 3 Drawing Sheets

OTHER PUBLICATIONS

Iwai, N. et al. (1994). "Molecular Variant of the Angiotensinogen Gene and Essential Hypertension in Japanese," Abstract 50 from unknown source.

Lu et al. (1994). "Cross–Sectional Analysis of Angiotensinogen Genotypes and Blood Pressures in Mexican Americans," Abstract 51 from unknown source.

Rotimi, C. et al. (1994). "Angiotensinogen Gene in Human Hypertension." Hypertension 24:591–594.

Hegele, R.A. et al. (1994). "A Polymorphism of the Angiotensinogen Gene Associated with Variation in Blood Pressure in a Genetic Isolate." Circulation 90:2207–2212.

Arngrimsson, R. et al. (1993). "Angiotensinogen: a candidate gene involved in preeclampsia." Nature Genetics 4:114–115.

Rutledge, D.R. et al. (1994). "Analysis of Two Variants of the Angiotensinogen Gene in Essential Hypertensive African–Americans." Am. J. Hypertension 7:651–654.

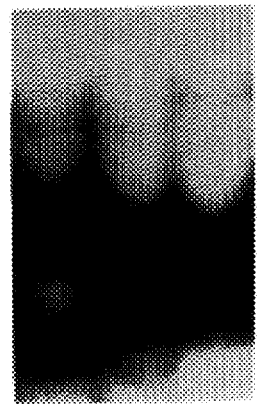
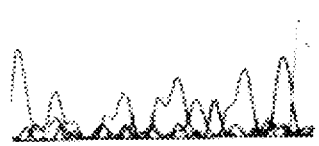
T174M
GCCCACCACCGTGGACA
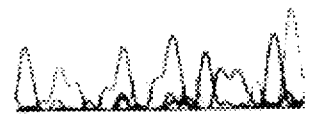
GCCCACCACCATGGACA
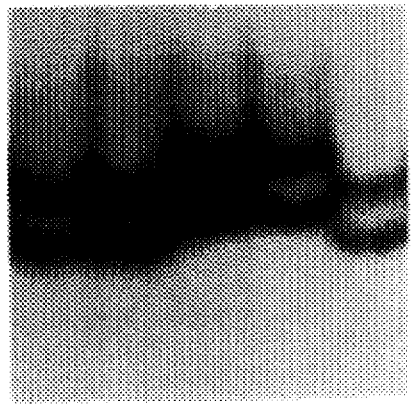
M235T
TGGCTCCCATCAG
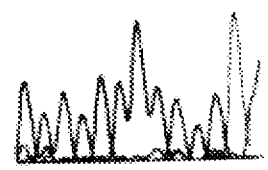
TGGCTCCCGTCAG
FIG. 2A  FIG. 2B

METHOD TO DETERMINE PREDISPOSITION TO HYPERTENSION

CROSS-REFERENCE TO RELATED APPLICATION

The present application is a continuation-in-part of application Ser. No. 07/952,442, filed on 30 Sep. 1992 issued as U.S. Pat. No. 5,374,525.

This invention was made with Government support under Grant Nos. HL24855 and HL45325, awarded by the National Institutes of Health, Bethesda, Md. The United States Government has certain rights in the invention.

BACKGROUND OF THE INVENTION

The present invention relates to molecular variants of the angiotensinogen gene. The present invention further relates to the diagnosis of these variants for the determination of a predisposition to hypertension and the management of hypertension.

The publications and other materials used herein to illuminate the background of the invention, or provide additional details respecting the practice, are incorporated by reference and for convenience are respectively grouped in the appended List of References.

Hypertension is a leading cause of human cardiovascular morbidity and mortality, with a prevalence rate of 25–30% of the adult Caucasian population of the United States (JNC Report, 1985). The primary determinants of essential hypertension, which represents 95% of the hypertensive population, have not been elucidated in spite of numerous investigations undertaken to clarify the various mechanisms involved in the regulation of blood pressure. Studies of large populations of both twins and adoptive siblings, in providing concordant evidence for strong genetic components in the regulation of blood pressure (Ward, 1990), have suggested that molecular determinants contribute to the pathogenesis of hypertension. However, there is no information about the genes actually involved, about the importance of their respective effects on blood pressure, or about their interactions with each other and the environment.

Among a number of factors for regulating blood pressure, the renin-angiotensin system plays an important role in salt-water homeostasis and the maintenance of vascular tone; stimulation or inhibition of this system respectively raises or lowers blood pressure (Hall and Guyton, 1990), and may be involved in the etiology of hypertension. The renin-angiotensin system includes the enzymes renin and angiotensin-converting enzyme and the protein angiotensinogen (AGT). Angiotensinogen is the specific substrate of renin, an aspartyl protease. The structure of the AGT gene has been characterized (Guillard et al., 1989; Fukamizu et al., 1990).

The human AGT gene contains five exons and four introns which span 13 Kb. The first exon (37 bp) codes for the 5' untranslated region of the mRNA. The second exon codes for the signal peptide and the first 252 amino acids of the mature protein. Exons 3 and 4 are shorter and code for 90 and 48 amino acids, respectively. Exon 5 contains a short coding sequence (62 amino acids) and the 3'-untranslated region.

Plasma angiotensinogen is primarily synthesized in the liver under the positive control of estrogens, glucocorticoids, thyroid hormones, and angiotensin II (Clauser et al., 1989) and is secreted through the constitutive pathway. Cleavage of the amino-terminal segment of angiotensinogen by resin releases a decapeptide prohormone, angiotensin-I, which is further processed to the active octapeptide angiotensin II by the dipeptidyl carboxypeptidase angiotensin-converting enzyme (ACE). Cleavage of angiotensinogen by renin is the rate-limiting step in the activation of the renin-angiotensin system (Sealey and Laragh, 1990). Several observations point to a direct relationship between plasma angiotensinogen concentration and blood pressure: (1) a direct positive correlation (Walker et al., 1979); (2) high concentrations of plasma angiotensinogen in hypertensive subjects and in the offspring of hypertensive parents compared to normotensives (Fasola et al., 1968); (3) association of increased plasma angiotensinogen with higher blood pressure in offspring with contrasted parental predisposition to hypertension (Watt et al., 1992); (4) decreased or increased blood pressure following administration of angiotensinogen antibodies (Gardes et al., 1982) or injection of angiotensinogen (Ménard et al., 1991); (5) expression of the angiotensinogen gene in tissues directly involved in blood pressure regulation (Campbell and Habener, 1986); and (6) elevation of blood pressure in transgenic animals overexpressing angiotensinogen (Ohkubo et al., 1990; Kimura et al., 1992).

Recent studies have indicated that renin and ACE are excellent candidates for association with hypertension. The human renin gene is an attractive candidate in the etiology of essential hypertension: (1) renin is the limiting enzyme in the biosynthetic cascade leading to the potent vasoactive hormone, angiotensin II; (2) an increase in renin production can generate a major increase in blood pressure, as illustrated by renin-secreting tumors and renal artery stenosis; (3) blockade of the renin-angiotensin system is highly effective in the treatment of essential hypertension as illustrated by angiotensin I-converting enzyme inhibitors; (4) genetic studies have shown that renin is associated with the development of hypertension in some rat strains (Rapp et al. 1989; Kurtz et al. 1990); (5) transgenic animals bearing either a foreign renin gene alone (Mullins et al. 1990) or in combination with the angiotensinogen gene (Ohkubo et al. 1990) develop precocious and severe hypertension.

The human ACE gene is also an attractive candidate in the etiology of essential hypertension. ACE inhibitors constitute an important and effective therapeutic approach in the control of human hypertension (Sassaho et al. 1987) and can prevent the appearance of hypertension in the spontaneously hypertensive rat (SHR) (Harrap et al., 1990). Recently, interest in ACE has been heightened by the demonstration of linkage between hypertension and a chromosomal region including the ACE locus found in the stroke-prone SHR (Hilbert et al., 1991; Jacob et al., 1991).

The etiological heterogeneity and multifactorial determination which characterize diseases as common as hypertension expose the limitations of the classical genetic arsenal. Definition of pheno-type, model of inheritance, optimal familial structures, and candidate-gene versus general-linkage approaches impose critical strategic choices (Lander and Botstein, 1986; White and Lalouel, 1987; Lander and Botstein, 1989; Lalouel, 1990, 1990; Lathrop and Lalouel, 1991). Analysis by classical likelihood ratio methods in pedigrees is problematic due to the likely heterogeneity and the unknown mode of inheritance of hypertension. While such approaches have some power to detect linkage, their power to exclude linkage appears limited. Alternatively, linkage analysis in affected sib pairs is a robust method which can accommodate heterogeneity and incomplete penetrance, does not require any a priori formulation of the mode of inheritance of the trait and can be used to place upper limits on the potential magnitude of effects exerted on a trait by inheritance at a single locus. (Blackwelder and Elston, 1985; Suarez and Van Eerdewegh, 1984).

It was an object of the present invention to determine a genetic association with essential hypertension. It was a further object to utilize such an association to identify persons who may be predisposed to hypertension leading to better management of the disease.

SUMMARY OF THE INVENTION

The present invention relates to the identification of a molecular basis of human hypertension. More specifically, the present invention has identified that angiotensinogen (AGT) is involved in the pathogenesis of hypertension. Molecular variants of the AGT gene contribute to an individual's susceptibility to the development of hypertension. The analysis of the AGT gene will identify subjects with a genetic predisposition to develop essential hypertension or pregnancy-induced hypertension. The management of hypertension in these subjects could then be more specifically managed, e.g., by dietary sodium restriction, by carefully monitoring blood pressure and treating with conventional drugs, by the administration of renin inhibitors or by the administration of drugs to inhibit the synthesis of AGT. The analysis of the AGT gene is performed by comparing the DNA sequence of an individual's AGT gene with the DNA sequence of the native, non-variant AGT gene.

BRIEF DESCRIPTION OF THE FIGURES

FIGS. 2A and 2B. Identification and DNA sequence analysis of variants in the angiotensinogen gene. Segments of the angiotensinogen gene were amplified and fractionated via electrophoresis on non-denaturing gels as described in the Examples. Autoradiograms showing the products of amplification of different hypertensive subjects are shown.

FIG. 2A shows products of an individual homozygous for the T174M variant (indicated by arrow) and two subjects homozygous for T174. Sequences of these different products were determined as described in the Examples and are shown below, with the T174 sequence shown above the corresponding T174M sequence (sequences are of the antisense strand with 5' to 3' orientation from left to right). The nucleotide substitution distinguishing the variants is indicated by *.

FIG. 2B shows products of two individuals homozygous for M235T (indicated by arrows) and three subjects homozygous for M235. The corresponding sequences are again shown below.

DETAILED DESCRIPTION OF THE INVENTION

Figure 1:
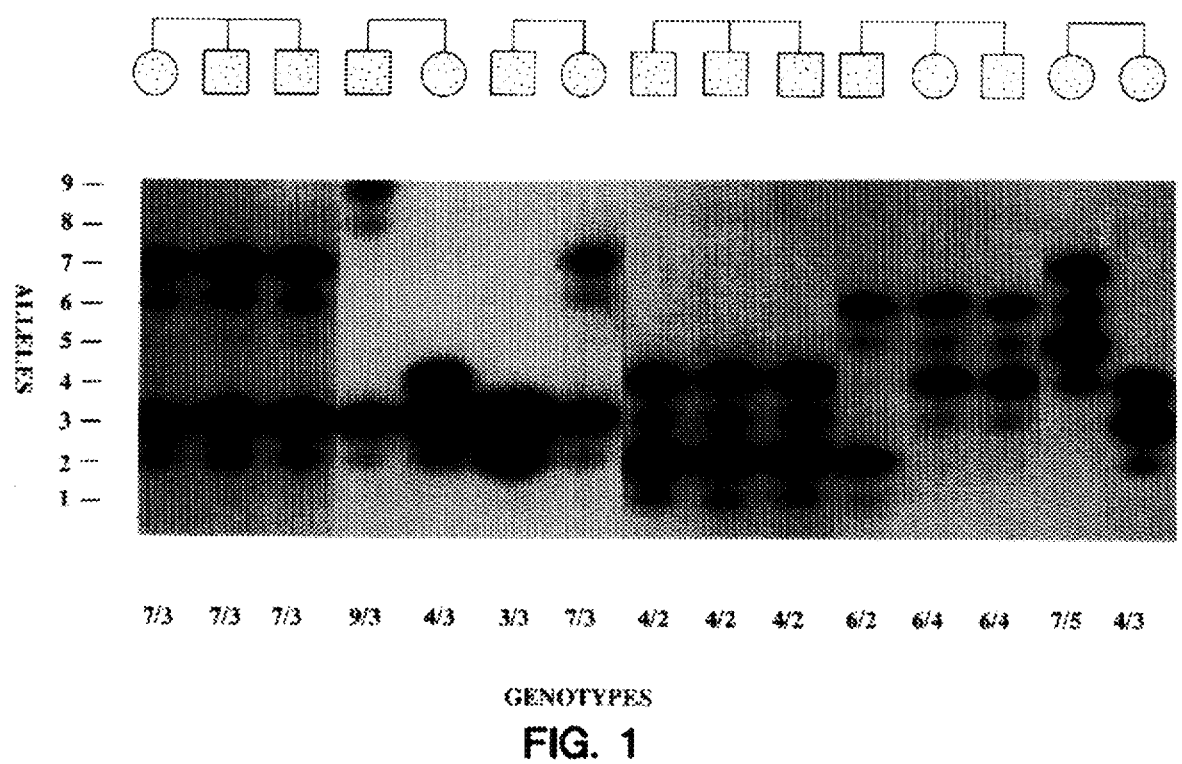
FIG. 1. Genotyping with a dinucleotide repeat at the angiotensinogen locus in hypertensive sibships. Representative genotypes for the AGT GT repeat are shown. Familial relationships in six hypertensive sibships are shown at the top of the figure. Genomic DNA of each individual was amplified with primers for the GT repeat at the AGT locus, fractionated via electrophoresis and subjected to autoradiography as described in the Examples; results for each individual are shown below, with assigned genotypes for each individual indicated at the bottom of the figure. Each allele characteristically shows a single dark band and a fainter band which is shorter by 2 base pairs; alleles have been scored according to the darker band.

The present invention is directed to the determination that molecular variants of the angiotensinogen (AGT) gene are involved in the pathogenesis of hypertension. The present invention has surprisingly found that molecular variants of the AGT gene contribute to the development of hypertension in humans. The present invention is further directed to methods of screening humans for the presence of AGT gene variants which are associated with the predisposition of humans to develop essential hypertension or pregnancy-induced hypertension. Since a predisposition to hypertension can now be established by screening for molecular variants of the AGT gene, individuals at risk can be more closely monitored and treated before the disease becomes serious.

Essential hypertension is one of the leading causes of human cardiovascular morbidity and mortality. Epidemiological studies of blood pressure in related individuals suggest a genetic heritability around 30% (Ward, 1990) The continuous, unimodal distribution of blood pressure in the general population as well as in the offspring of hypertensive parents (Hamilton et al., 1954) supports the hypothesis that several genes are involved in this genetic predisposition. However, there is no information about the genes actually involved, about the importance of their respective effects on blood pressure, or their interactions with each other and the environment.

Genetic studies in animal models of hypertension have suggested an involvement of the two key enzymes of this system in the genesis of high blood pressure, renin (Rapp et al., 1989; Mullins et al., 1990; Kurtz et al., 1990), and angiotensin converting enzyme through linkage to a nearby marker (Hilbert et al., 1991; Jacob et al., 1991; Deng and Rapp, 1992). The purpose of the present invention was to identify an association with hypertension. It was unexpectedly found that neither renin nor angiotensin-converting enzyme is associated with human hypertension. Instead, it was found that the angiotensinogen gene is involved in the pathogenesis of essential hypertension. The following were found: (1) genetic linkage between essential hypertension and AGT in affected siblings; (2) association between hypertension and certain molecular variants of AGT as revealed by a comparison between cases and controls; (3) increased concentrations of plasma angiotensinogen in hypertensive subjects who carry a common variant of AGT strongly associated with hypertension; (4) persons with the most common AGT gene variant exhibited not only raised levels of plasma angiotensinogen but also higher blood pressure; and (5) the most common AGT gene variant was found to be statistically increased in women presenting preeclampsia during pregnancy, a condition occurring in 5–10% of all pregnancies.

The association between renin, ACE or AGT and essential hypertension was studied using the affected sib pair method (Bishop and Williamson, 1990) on populations from Salt Lake City, Utah and Paris, France, as described in further detail in the Examples. Only an association between the AGT gene and hypertension was found. The AGT gene was examined in persons with hypertension, and at least 15 variants have been identified. None of these variants occur in the region of the AGT protein cleaved by either renin or ACE. The identification of the AGT gene as being associated with essential hypertension was confirmed in a population study of healthy subjects and in women presenting preeclampsia during pregnancy.

Although molecular variants of the AGT gene have been established as predisposing a person to hypertension, it is not possible to determine at this time whether the observed molecular variants of AGT directly affect function or whether they serve as markers for functional variants that have escaped identification by the molecular screening method used. When the sequence of human angiotensinogen is compared to that of rat angiotensinogen, and to other serine protease inhibitors (serpins) such as antithrombin-III and alpha-1-antitrypsin, the AGT gene variants M235T and T174M appear to occur in regions with little conservation (Carrell and Boswell, 1986). By contrast, the variant Y248C, which was observed in the heterozygote state in only one pair of hypertensive siblings, constitutes a non-conservative substitution in a region well conserved among serpins. In addition to this predisposition encoded by common variants, rare variants such as Y248C and V388M have the potential to impart predispositions with unique clinical courses and severities.

As used herein, AGT gene variants are expressed either at the amino acid level, e.g., M235T in which the variant protein contains threonine at amino acid residue 235 instead of methionine, or at the nucleotide level, e.g., C-532T in which the variant gene contains thymidine at nucleotide −532 of the 5' sequence instead of cytosine of the native gene. Several mutations are set forth in Table 2.

When hypertensive siblings were stratified according to genotypes at residue 235, higher plasma concentrations of angiotensinogen were observed among carriers of M235T ($F_{2,313}=14.9$, $p<0.0001$). Again, this result was observed independently in each sample. A correlation between plasma angiotensinogen concentration and blood pressure has already been observed (Walker et al., 1979). Taken together, these observations suggest a direct involvement of plasma angiotensinogen in the pathogenesis of essential hypertension. This conclusion is further strengthened by finding that the M235T variant was significantly associated not only with raised plasma angiotensinogen concentrations but also with increased blood pressure. See Example 8, below. The present invention is corroborated by two additional findings: (1) plasma angiotensinogen was higher in hypertensive subjects and in the offspring of hypertensive parents than in normotensives (Fasola et al., 1968); and (2) in the Four-Corners study, angiotensinogen concentrations were significantly associated with increased blood pressure in the subset most likely to entail a genetic predisposition, namely the high-blood pressure offspring of high-blood pressure parents (Watt et al., 1992). Because the plasma concentration of angiotensinogen is close to the $K_m$ of the enzymatic reaction between renin and angiotensinogen (Gould and Green, 1971), a rise or fall in renin substrate can lead to a parallel change in the formation of angiotensin II (Cain et al., 1971; Ménard and Catt, 1973; Arnal et al., 1991). Therefore, it is conceivable that raised baseline levels could lead to mild overactivity of the renin-angiotensin system, and represent an altered homeostatic setpoint in predisposed individuals. Indeed, long-term administration of angio-tensin II at subpressor doses has been shown to elevate blood pressure (Brown et al., 1981).

Recent studies suggest that not only plasma angiotensinogen, but also local expression in specific tissues, could contribute to blood pressure regulation. Yongue et al. (1991) observed increased expression of angiotensinogen in the anteroventral hypothalamus and in contiguous areas of the brain in SHR rats in comparison to normotensive control WKY rats, but they found no difference in liver expression. A possible role of angiotensinogen in the central nervous system is further supported by experimental overexpression of the AGT gene in transgenic rats: plasma concentrations were raised, but high blood pressure was observed only in a transgenic line displaying proper tissue-specific expression of the transgene in the brain (Kimura et al., 1992). Furthermore, evidence for local synthesis of the different components of the renin angiotensin system in the kidney has accumulated and an alteration of the regulation of angiotensinogen expression by sodium has been observed in SHR rats (Pratt et al., 1989).

Without being bound by any theory of action, it is possible that some molecular variants of angiotensinogen, such as those identified or tagged by the variant at residue 235 or the variant at the −6 nucleotide, lead to increased plasma or tissue angiotensinogen as a result of either increased synthetic rate, altered reaction constants with renin, or increased residence time through complex formation with self or with other extracellular proteins. This could lead to a small increase in baseline or in reactive production of angiotensin II, accounting for a slight overreactivity of the renin-angiotensin system in response to sodium and environmental stressors. Over decades, this in turn could promote sodium retention as a result of chronic stimulation of aldosterone secretion, vascular hypertrophy and increased peripheral vascular resistance as a result of chronic elevation of angiotensin II formation, or abnormal stimulation of the sympathetic nervous system mediated by enhanced production of angiotensin II in relevant areas of the brain.

The identification of the association between the AGT gene and hypertension permits the screening of individuals to determine a predisposition to hypertension. Those individuals who are identified at risk for the development of the disease may benefit from dietary sodium restriction, can have their blood pressure more closely monitored and be treated at an earlier time in the course of the disease. Such blood pressure monitoring and treatment may be performed using conventional techniques well known in the art.

To identify persons having a predisposition to hypertension, the AGT alleles are screened for mutations. Plasma angiotensinogen levels of persons carrying variants of the AGT gene are then examined to identify those at risk. Any human tissue can be used for testing the DNA. Most simply, blood can be drawn and DNA extracted from the cells of the blood. The AGT alleles are screened for mutations either directly or after cloning the alleles.

The alleles of the AGT gene in an individual to be tested are cloned using conventional techniques. For example, a blood sample is obtained from the individual. The genomic DNA isolated from the cells in this sample is partially digested to an average fragment size of approximately 20 kb. Fragments in the range from 18–21 kb are isolated. The resulting fragments are ligated into an appropriate vector. The sequences are then analyzed as described herein.

Alternatively, polymerase chain reactions (PCRs) are performed with primer pairs for the 5' region or the exons of the AGT gene. Examples of such primer pairs are set forth in Table 1. PCRs can also be performed with primer pairs based on any sequence of the normal AGT gene. For example, primer pairs for the large intron can be prepared and utilized. Finally, PCR can also be performed on the mRNA. The amplified products are then analyzed as described herein.

on a large number of samples. An example of a mismatch cleavage technique is the RNase protection method. In the practice of the present invention, the method involves the use of a labeled riboprobe which is complementary to the human wild-type AGT gene coding sequence. The riboprobe and either mRNA or DNA isolated from the tumor tissue are

TABLE 1

Primers Used for the Detection of Molecular Variants of AGT

| Location | Primer 1 (SEQ ID NO:) | Primer 2 (SEQ ID NO:) |
|---|---|---|
| 5' | ACCATTTGCAATTTGTACAGC (1) | GCCCGCTCATGGGATGTG (2) |
| 5' | AAGACTCTCCCCTGCCCCTCT (3) | GAAGTCTTAGTGATCGATGCAG (4) |
| 5' + Ex1 | AGAGGTCCCAGCGTGAGTGT (5) | AGACCAGAAGGAGCTGAGGG (6) |
| Ex2 | GTTAATAACCACCTTTCACCCTT (7) | GCAGGTATGAAGGTGGGGTC (8) |
| Ex2 | AGGCCAATGCCGGGAAGCCC (9) | ATCAGCCCTGCCCTGGGCCA (10) |
| Ex2 | GATGCGCACAAGGTCCTGTC (11) | GCCAGCAGAGAGGTTTGCCT (12) |
| Ex3 | TCCCTCCCTGTCTCCTGTCT (13) | TCAGGAGAGTGTGGCTCCCA (14) |
| Ex4 | TGGAGCCTTCCTAACTGTGC (15) | AGACACAGGCTCACACATAC (16) |
| Ex5 | GTCACCCATGCGCCCTCAGA (17) | GTGTTCTGGGGCCCTGGCCT (18) |

The alleles are tested for the presence of nucleic acid sequence differences from the normal allele by determining the nucleotide sequence of the cloned allele or amplified fragment and comparing it to the nucleotide sequence of the normal allele. Alternatively, there are six well known methods for a more complete, yet still indirect, test for confirming the presence of a predisposing allele: 1) single stranded conformation analysis (SSCA) (Orita et al., 1989); 2) denaturing gradient gel electrophoresis (DGGE) (Wartell et al., 1990; Sheffield et al., 1989); 3) RNase protection assays (Finkelstein et al., 1990; Kinszler et al., 1991); 4) allele-specific oligonucleotides (ASOs) (Conner et al., 1983); 5) the use of proteins which recognize nucleotide mismatches, such as the E. coli mutS protein (Modrich, 1991); and, 6) allele-specific PCR (Rano & Kidd, 1989). For allele-specific PCR, primers are used which hybridize at their 3' ends to a particular AGT mutation. If the particular AGT mutation is not present, an amplification product is not observed. Amplification Refractory Mutation System (ARMS) can also be used, as disclosed in European Patent Application Publication No. 0332435 and in Newton et al., 1989.

In the first three methods (SSCA, DGGE and RNase protection assay), a new electrophoretic band appears. SSCA detects a band which migrates differentially because the sequence change causes a difference in single-strand, intramolecular base pairing. RNase protection involves cleavage of the mutant polynucleotide into two or more smaller fragments. DGGE detects differences in migration rates of mutant sequences compared to wild-type sequences, using a denaturing gradient gel. In an allele-specific oligonucleotide assay, an oligonucleotide is designed which detects a specific sequence, and the assay is performed by detecting the presence or absence of a hybridization signal. In the mutS assay, the protein binds only to sequences that contain a nucleotide mismatch in a heteroduplex between mutant and wild-type sequences.

Mismatches, according to the present invention, are hybridized nucleic acid duplexes in which the two strands are not 100% complementary. Lack of total homology may be due to deletions, insertions, inversions or substitutions. Mismatch detection can be used to detect point mutations in the gene or in its mRNA product. While these techniques are less sensitive than sequencing, they are simpler to perform annealed (hybridized) together and subsequently digested with the enzyme RNase A which is able to detect some mismatches in a duplex RNA structure. If a mismatch is detected by RNase A, it cleaves at the site of the mismatch. Thus, when the annealed RNA preparation is separated on an electrophoretic gel matrix, if a mismatch has been detected and cleaved by RNase A, an RNA product will be seen which is smaller than the full length duplex RNA for the riboprobe and the mRNA or DNA. The riboprobe need not be the full length of the AGT mRNA or gene but can be a segment of either. If the riboprobe comprises only a segment of the AGT mRNA or gene, it will be desirable to use a number of these probes to screen the whole mRNA sequence for mismatches.

In similar fashion, DNA probes can be used to detect mismatches, through enzymatic or chemical cleavage. See, e.g., Cotton et al., 1988; Shenk et al., 1975; Novack et al., 1986. Alternatively, mismatches can be detected by shifts in the electrophoretic mobility of mismatched duplexes relative to matched duplexes. See, e.g., Cariello, 1988. With either riboprobes or DNA probes, the cellular mRNA or DNA which might contain a mutation can be amplified using PCR before hybridization. Changes in DNA of the AGT gene can also be detected using Southern hybridization, especially if the changes are gross rearrangements, such as deletions and insertions.

DNA sequences of the AGT gene which have been amplified by use of PCR may also be screened using allele-specific probes. These probes are nucleic acid oligomers, each of which contains a region of the AGT gene sequence harboring a known mutation. For example, one oligomer may be about 30 nucleotides in length, corresponding to a portion of the AGT gene sequence. By use of a battery of such allele-specific probes, PCR amplification products can be screened to identify the presence of a previously identified mutation in the AGT gene. Hybridization of allele-specific probes with amplified AGT sequences can be performed, for example, on a nylon filter. Hybridization to a particular probe under stringent hybridization conditions indicates the presence of the same mutation in the DNA sample as in the allele-specific probe.

Mutations falling outside the coding region of AGT can be detected by examining the non-coding regions, such as introns and regulatory sequences near or within the AGT gene. An early indication that mutations in noncoding regions are important may come from Northern blot experiments that reveal messenger RNA molecules of abnormal size or abundance in hypertensive patients as compared to control individuals.

Alteration of AGT mRNA expression can be detected by any techniques known in the art. These include Northern blot analysis, PCR amplification and RNase protection. Diminished mRNA expression indicates an alteration of the wild-type AGT gene. Alteration of wild-type AGT genes can also be detected by screening for alteration of wild-type angiotensinogen. For example, monoclonal antibodies immunoreactive with angiotensinogen can be used to screen a tissue. Lack of cognate antigen would indicate a AGT gene mutation. Antibodies specific for products of mutant alleles could also be used to detect mutant AGT gene product. Such immunological assays can be done in any convenient formats known in the art. These include Western blots, immunohistochemical assays and ELISA assays. Any means for detecting an altered angiotensinogen can be used to detect alteration of wild-type AGT genes. Finding a mutant AGT gene product indicates alteration of a wild-type AGT gene.

Further details of a suitable PCR method are set forth in the Examples. The AGT alleles can be screened for the variants set forth in Table 2, as well as other variants using these techniques or those techniques known in the art.

EXAMPLE 1

Selection of Sibships with Multiple Hypertensive Subjects

A. Salt Lake City. Families with two or more hypertensive siblings were characterized and sampled from "Health Family Tree" questionnaires collected from the parents of 40,000 high school students in Utah. The characteristics of this population-based selection of hypertensive sibships have been described previously (Williams et al., 1988). For purposes of the present study, affection status was defined as a diagnosis of hypertension requiring treatment with antihypertensive medication prior to age 60, and the absence of diabetes mellitus or renal insufficiency; the study sample comprises 309 siblings (165 women, 144 men). All but three sibling pairs were Caucasians (one was Asian, two Hispanic) and their relevant clinical characteristics are indicated in Table 3. The 132 affected sibships are composed of 102 duos, 20 trios, seven quartets, one quintet, and two sextets of hypertensive siblings.

B. Paris. The selection of hypertensive families with a high prevalence of essential hypertension was conducted through ascertainment of hypertensive probands referred to the Hypertension Clinic of the Broussais Hospital in Paris, as previously described (Corvol et al., 1989). The 83 French sibships were collected through index patients who satisfied the following criteria: (1) onset of hypertension before age

TABLE 2

Molecular Variants in the Angiotensinogen Gene

| | | | Substitution | | Allele Frequency | |
|---|---|---|---|---|---|---|
| | | | | | Salt Lake City[1] | Paris[2] |
| Variant | Location | Position[3] | Nucleotide | Amino Acid | H/C | H/C |
| 1 | 5' | −532 | C → T | | .13/.12 | .11/n.d; |
| 2 | 5' | −386 | G → A | | .04/.04 | .02/n.d. |
| 3 | 5' | −218 | G → A | | .11/.10 | .08/n.d. |
| 4 | 5' | −18 | C → T | | .13/.13 | .19/n.d. |
| 5 | 5' | −6 and −20 | G → A and A → C | | .19/.14 | .18/n.d. |
| 6 | Ex1 | +10 | C → T | untranslated | 1 ind/0 | 0/n.d. |
| 7 | Ex2 | +521 | C → T | T → M (174) | .18/.08[4] | .17/.08[4] |
| 8 | Ex2 | +597 | T → C | P → P (199) | 1 ind/0 | 0/n.d. |
| 9 | Ex2 | +704 | T → C | M → T (235) | .49/.36[5] | .52/.38[4] |
| 10 | Ex2 | +743 | A → G | Y → C (248) | 1 ind/0 | 0/n.d. |
| 11 | Ex3 | +813 | C → T | N → N (271) | 1 ind/0 | 0/0 |
| 12 | Ex3 | +1017 | G → A | L → L (339) | .05/.08 | .06/n.d. |
| 13 | Int3 | −13[6] | A → G | | .07/.11 | .08/n.d. |
| 14[7] | Ex4 | +1075 | C → A | L → M (359) | .005/.01n.d./n.d. | |
| 15 | Ex4 | +1162 | G → A | V → M (388) | 0/0 | 0/1 ind |

[1]Salt Lake City: 90 controls, 36 index patients from most severely affected pairs.
[2]Paris: 98 controls, 43 index patients from most severely affected pairs.
[3]Position is with reference to transcription start site.
[4]$p < 0.01$
[5]$p < 0.05$
[6]Position relative to beginning of exon 4.
[7]Variant previously described suppressing a PstI site (Kunapuli and Kumer, 1986).
H/C Hypertensive/Control
n.d. not done.
1 ind 1 individual detected with the corresponding molecular variant.

The present invention is further detailed in the following Examples, which are offered by way of illustration and are not intended to limit the invention in any manner. Standard techniques well known in the art or the techniques specifically described below are utilized.

60; (2) established hypertension defined either by chronically treated hypertension (n=156) or by a diastolic blood pressure greater than 95 mmHg at two consecutive visits for those without antihypertensive treatment (n=34, mean diastolic blood pressure=103.8±13.1 mmHg); (3) absence of secondary hypertension, established by extensive inpatient work-up when clinically indicated; and (4) familial history of early onset (before age 60) of hypertension in at least one parent and one sibling. Patients with exogenous factors that could influence blood pressure were eliminated, in particular those with alcohol intake of more than four drinks per day or women taking oral contraceptives. Other exclusion criteria were a body mass index (BMI=weight/height$^2$) greater than 30 kg/m$^2$, the presence of diabetes mellitus, or renal insufficiency; the total sample consisted of 83 hypertensive sibships with 62 duos, 19 trios, 1 quartet and 1 quintet. All subjects were Caucasians and their relevant clinical characteristics are summarized in Table 3, below.

C. Controls. In Salt Lake City, 140 controls were defined as the grandparents of the Utah families included in the CEPH data base (Centre d'Etude du Polymorphisme Humain), a random panel of healthy families with large sibship size that serves as reference for linkage studies (Dausset et al., 1990). The French controls were 98 healthy normotensive subjects who had been selected in the context of a previous case-control study (Soubrier et al., 1990). Both samples included only Caucasians.

TABLE 3

Clinical Characteristics
of the Hypertensive Siblings

| | Salt Lake City | Paris |
|---|---|---|
| Sibships (pairs) | 132 (244) | 83 (135) |
| Subjects (m/f) | 309 (144/165) | 190 (99/91) |
| Age (years) | 49.4 (±7.4) | 52.3 (±9.9) |
| Age dx (years) | 39.4 (±9.6) | 40.4 (±11.7) |
| SBP (mmHg) | 127.8 (±15.6) | 156.0 (±21.5) |
| DBP (mmHg) | 80.0 (±9.9) | 98.2 (±12.6) |
| Rx (%) | 309 (100%) | 158 (82%) |
| B.M.I. (Kg/m$^2$) | 29.7 (±5.5) | 24.9 (±3.0) |

Age dx: Age of diagnosis
SBP and DBP: Systolic and Diastolic Blood Pressure
B.M.I.: Body Mass Index
Unless otherwise stated, values are indicated as mean ± 1 S.D.

EXAMPLE 2

General Methods for Analysis of Linkage with Renin

A. Experimental Protocols

The experimental protocols using the French populations were conducted as previously described (Soubrier et al. 1990). Briefly, two probes were used to detect the diallelic RFLPs of three restriction enzymes. A 1.1-kb human renin cDNA fragment (Soubrier et al. 1983) was used to detect the HindIII polymorphism and a 307-bp genomic DNA fragment located in the 5' region of the renin gene (Soubrier et al. 1986) was used to detect the TaqI and HinfI polymorphisms. These two probes were labeled at high specific activity ($4 \times 10^9$ to $8 \times 10^9$ cpm/mg) with the random primer labelling method (Feinberg and Vogelstein 1983).

Human genomic DNA was digested by TaqI, HinfI, or HindIII (New England Biolabs, Beverly, Mass.) and subjected to electrophoresis through an agarose gel (0.7% or 1.2%). After alkaline transfer to a nylon membrane (Hybond-N+, Amersham), hybridization to the corresponding probe, washing under high stringency conditions, and autoradiography, each restriction endonuclease detected the following biallelic RFLPs: 11- and 9.8-kb alleles (TaqI), 1.4- and 1.3-kb alleles (HinfI), and 9.0- and 6.2-kb alleles (HindIII). These polymorphisms and their frequencies were in accordance with those previously described (Frossard et al., 1986 a,b; Masharani, 1989; Naftilan et al., 1989).

B. Analysis of RFLP Frequencies

For each RFLP, allele frequencies were determined from the genotype frequencies that had been previously established in 120 normotensives and 102 hypertensives (Soubrier et al. 199). These frequencies satisfied the Hardy-Weinberg equilibrium. The informativeness of each biallelic RFLP, estimated by the polymorphism information content (PIC), was respectively 0.16 (TaqI), 0.33 (HindIII), and 0.27 (HinfI). In spite of linkage disequilibriums between the HinfI-HindIII and HinfI-TaqI polymorphisms, the combination of the three RFLPs led to a marked improvement in the marker's informativeness (PIC=0.65), corresponding to 70% of heterozygosity.

C. Construction of Haplotypes

The haplotypes were deduced from the combination of the three diallelic RFLPs. By the presence or absence of each restriction enzyme site, it was possible to define 8 ($2^3$) different haplotypes and 27 ($3^3$) genotypes. The haplotype frequencies have been previously estimated on a hypertensive population (Soubrier et al. 1990), with a maximum likelihood technique according to Hill's method (Hill 1975). These haplotypes were used as a new multiallelic system in which each allele corresponded to one haplotype, numbered by its order frequency. These frequencies enabled us to compute the expected values of the number of alleles shared by a sibship under the hypothesis of an independent segregation of the renin gene marker and hypertension.

D. Comparison of Sib Genotypes

In 12 sibships, it was not possible to determine with certainty each haplotype—the presence of double or triple heterozygosity in the restriction enzyme sites—in spite of the analysis of other members of the same family. In these cases, the relative different parental mating type probabilities were calculated according to the haplotype frequencies. Then, the probabilities of the genotypes of each sib pair were deduced conditional to each parental mating type. For each sibship, the concordance between sibs was calculated as the mean of all possible concordances according to their relative probabilities.

Because of the absence of one or two parental genotypes in 40 of the 57 sibships, and of the absence of complete heterozygosity of the renin marker, the alleles shared in common by one sib pair were assumed to be identical by state (ibs), rather than identical by descent. The concordance between the sib genotypes could be total (ibs=1), partial (ibs=½), or absent (ibs=0). Under the null hypothesis of no linkage, the mean number of identical market alleles shared by a set of sib pairs (and its variance) is not affected by whether or not some of the sib pairs belong to the same sibship (Suarez et al. 1983, Blackwelder and Elston 1985). Thus, the renin genotypes were compared for each sib pair and all the information contained in each sibship was taken into account by adding the concordances between all different sib pairs.

E. Comparison of the Expected Concordance Values

The expected proportions of alleles shared by both sibs were computed according to Lange (1986). This statistical method first calculates the probabilities of the different possible parental mating types taking into account the allelic frequencies and then the expected probabilities of total, half, or null concordance between sibs. It is thus possible to calculate the mean and the variance of the expected concordance for different sibship sizes under the null hypothesis of no linkage. The final t statistic is a one-sided Student's test adding the contributions of the different sibships.

Taking into account the possible bias in ascertainment of the size of the sibships, several authors have proposed different weights (w) to maximize the power of this statistic. In addition to $w_1=1$, we tested $w_2=1/\text{Var}(Z_s)^{1/2}$ (Suarex et al. 1983; Motro and Thompson 1985) and $w_3=(s-1)^{1/2}/\text{Var}(Z_s)^{1/2}$ (Hodge 1984), where s represents the size of the affected sibship and Z, the statistic reflecting the allelic concordance for each sibship size (Lange 1986).

EXAMPLE 3

General Methods for Analysis of Linkage with ACE

A. Genotypes (1) The hGH-A1819 primers were designed from the published sequence flanking the eighteenth and nineteenth Alu elements of the hGH gene (Chen et al., 1989): 5'-ACTGCACTCCAGCCTCGGAG-3' (SEQ ID NO: 19), 5'-ACAAAAGTCCTTTCTCCAGAGCA-3' (SEQ ID NO:20). Polymerase chain reactions (PCR) were performed using 100 ng of genomic DNA in a total volume of 20 ml containing 1×PCR Buffer (Cetus), 125 mM dNTPs, 150 pmol primers, 2 mCia 32P-dCTP. After an initial denaturation step (4 min at 94° C.), each of the 30 cycles consisted of 1 min at 94° C., 45 s at 63° C. and 30 s at 72° C., followed by a final elongation step (7 min at 72° C.). PCR reactions were performed in 96-well microtitre plates, using a Techne 2 apparatus. After completion, 20 ml of formamide with 10 mM EDTA was added to each reaction and, after denaturation of 94° C. for 5 min, 1 ml of this mixture was loaded on a 6% acrylamide gel containing 30% formamide, 7M Urea, 135 mM TrisHCl, 45 mM boric acid and 2.5 mM EDTA. Gels were run at 70 W for 4 hr and were exposed 6–12 hr for autoradiography. (2) The ACE diallelic polymorphism was genotyped by enzymatic amplification of a segment in intron 16, with the 190 and 490 bp alleles resolved by a 1.5% agarose gel (Rigat et al., 1992).

B. Genetic Mapping

The chromosome 17 markers used in the genetic map were developed in the Department of Human Genetics of the University of Utah (Nakamura et al., 1988). The pairwise lod scores and recombination estimates (r) were determined from the analysis of 35 and 11 CEPH reference families for the ACE and hGH markers, respectively, using LINKAGE. (Lathrop et al., 1984) No recombination between ACE and hGH was detected from this pairwise analysis. Map order and recombination estimates of the chromosome 17 markers have then been determined using the CILINK subroutine. The placement of ACE has been determined by linkage to this genetic map in which the order and recombination frequencies between all other markers, including hGH, have been fixed at their maximum likelihood values.

C. Sib Pair Analysis

All sib pairs from multiplex sibships were considered as independent, and the statistic was based on the mean number of alleles shared. (Blackwelder and Elston, 1985) In the absence of parental genotypes, the sharing of alleles was scored as i.b.s. For each sibship size, the expectation of the mean number of alleles shared i.b.s. and its variance were calculated as described previously. (Lange, 1986) The results show a 0.08% excess of alleles shared (95% confidence interval ±6.9%). For all pairs given equal weight, the one-sided t value is 0.02 (p=0.45). Weighting the contributions of multiplex sibships according to Hodge (Hodge, 1984) gives a final t value of 0.01 (p=0.49).

EXAMPLE 4

General Methods of Analysis of Linkage with AGT

A. Genotyping GT Alleles at the AGT Locus

AGT genotypes were established by means of a highly informative dinucleotide repeat in the 3' flanking region of the AGT gene (Kotelevtsev et al., 1991). The primers used for the Paris sample were as published (K-primers); for the genotypes characterized in Utah, primers more distant to the (GT) repeat were designed:

5'-GGTCAGGATAGATCTCAGCT-3' (SEQ ID NO:21),

5'-CACTTGCAACTCCAGGAAGACT-3' (SEQ ID NO:22)

(U-Primers), which amplify a 167-bp fragment. In both laboratories, the polymerase chain reactions (PCR) were performed using 80 ng of genomic DNA in a total volume of 20 µl containing 50 mM KCl, 5 mM Tris-HCl, 0.01% gelatin, 1.5 mmol $MgCl_2$, 125 µM dNTPs, 20 pmol of each unlabeled primer, 10 pmol of one $^{32}$P-end labeled primer and 0.5 U of Taq polymerase (Perkin-Elmer Cetus Norwalk, Conn.). After an initial denaturation step (4 min at 94° C.), each of the 30 cycles consisted of 1 min at 94° C., 1 min at 55° C. and 1 min at 72° C. (K-primers) or 45 sec at 94° C., 45 sec at 62° C. and 30 sec at 72° C. (U-primers). After completion, 20 µl of formamide with 10 mM EDTA was added to each reaction and, after denaturation at 94° C. for 5 min, 1 µl of this mixture was loaded on a 6% acrylamide gel containing 30% formamide, 7M Urea, 135 mM TrisHCl, 45 mM Boric Acid and 2.5 mM EDTA (pH 7.8). Gels were run at 70 W for 4 hours and were exposed 6–12 hours for autoradiography.

Genotypes were characterized in each of the hypertensive subjects and in 117 of their first-degree relatives. Allelic frequencies were evaluated in 98 Caucasian normotensive controls from Paris, 140 Caucasian grandparents of CEPH pedigrees from Salt Lake City, and both sets of hypertensive index cases. At least 10 alleles were observed in each of the four groups, confirming the high heterozygosity (80%) of the marker. No significant difference in allelic frequencies was observed between controls and hypertensives from Paris ($\chi^2_6=7.7$, p=0.26); frequencies in controls were used as reference for linkage analysis in this sample. By contrast, controls and hypertensives from Salt Lake City exhibited significant differences in allelic frequencies ($\chi^2_6=17.1$, p<0.01), primarily because the frequency of the most common allele was lower in hypertensives (0.36) than in controls (0.40); to avoid spurious bias on linkage tests, the frequencies estimated in hypertensive index cases were used for the analysis of the Salt Lake City sample.

B. Analysis of Linkage in Pairs of Hypertensive Siblings

Conditional independence of segregating events within sibships (Suarez and Van Eerdewegh, 1984) led to the generation of a total of 379 pairs of hypertensive siblings. Parental genotypes were determined directly or inferred from genotypes of non-hypertensive siblings in ten of the French sibships. In these sibships, alleles shared by siblings were considered as identical by descent (i.b.d.) and the appropriate statistical comparison employed (mean of 1.0 alleles shared per pair under independence). In the absence of parental genotypes (all Utah sibships, 73 French sibships), alleles shared by siblings were scored as identical by state (i.b.s) (Suarez et al., 1978; Blackwelder and Elston, 1985; Lange, 1986). For each sibship size, the expectation of the mean number of alleles shared i.b.s., and its variance, were calculated according to Lange (1986). The comparison between the observed and expected mean numbers of alleles shared by the pairs of siblings of every sibship yielded a one-sided Student t-test. The contribution of sibships of each size was weighted according to Hodge (Hodge, 1984). Predefined partitions of the data were examined sequentially so as to provide a parsimonious management of the degrees of freedom associated with multiple comparisons.

C. Search for Molecular Variants

Enzymatic amplification of segments of the angiotensinogen gene. From the known genomic structure of the human angiotensinogen gene (Gaillard et al., 1989), ten different sets of oligonucleotides (Table 1) were designed to cover the 5' region containing the main regulatory elements and the five exons of the gene. They were chosen so as to generate products 200–300 bp long that would include at least 15 bp of the intronic sequence on either side of splice junctions.

For the conformational analysis of single-stranded DNA, samples were enzymatically amplified using 80 ng of genomic DNA in a total volume of 20 µl containing 50 mM KCl, 5 mM Tris-HCl (pH 8.3), 0.01% gelatin, 1.5 mmol $MgCl_2$, 125 µM dNTPs, 20 pmol of each unlabeled primer, 0.5 U of Taq polymerase and 0.15 µl of [$\alpha$-$^{32}$P] dCTP (3000 Ci/ml).

Electrophoresis of DNA fragments under nondenaturing conditions. PCR products were diluted five-fold in a solution containing 95% formamide, 20 mM EDTA, 0.05% bromophenol blue, and 0.05% xylene cyanol. After denaturation at 90° C. for 4 min the samples were placed on ice, and 1.5 µl aliquots were loaded onto 5% nondenaturing polyacrylamide gels (49:1 polyacrylamide:methylene-bis acrylamide) containing 0.5×TBE (1×TBE=90 mM Trisborate, pH 7.8, 2 mM EDTA) (Orita et al, 1989). Each set of samples was electrophoresed under at least three conditions: a 10% glycerol gel at room temperature and at 4° C., and a gel without glycerol at 4° C. For the first, two conditions, electrophoresis was carried out at 500 Volts, constant voltage, for 14–20 hours; for the third, electrophoresis was performed at 15 W, constant power, for 4–5 hours. The gels were dried and autoradiographed with an intensifying screen for 6–12 hours.

Direct sequencing of electrophoretic variants. Individual bands that presented mobility shifts with respect to wild type were sequenced as described by Hata et al. (1990), with some modifications. Each band was excised from the dried gel, suspended in 100 µl $H_2O$, and incubated at 37° C. for 1 hr. A 2-µl aliquot was subjected to enzymatic amplification in a 100-µl reaction volume, with specific primers augmented at their 5' ends with motifs corresponding to universal and reverse M13 sequencing primers. The double-stranded product resulting from this amplification was isolated by electrophoresis on a low-melting agarose gel and purified using GeneClean (Bio 101, La Jolla, Calif.). A second round of enzymatic amplification was usually performed under similar conditions, using reduced amounts of primers (5 picomol) and of dNTPs (50 µM), and the amplified product was spin-dialyzed with a Centricon 100 column (Amicon, Beverly, Mass.)). Direct sequencing of double-stranded DNA was performed on an ABI 373A DNA sequencer, using fluorescent M13 primers, Taq polymerase and a thermocycling protocol supplied by the manufacturer (Applied Biosystems, Foster City, Calif.).

Allele-specific oligonucleotide hybridization. To verify the presence of molecular variants identified by direct sequencing and to determine genotypes, oligonucleotide-specific hybridization was performed. After enzymatic amplification of genomic DNA, each product was denatured with 0.4N NaOH for 5 min, then spotted in duplicate on nylon membranes (Hybond+, Amersham, Arlington Heights, Ill.), neutralized with 3M Na acetate and cross-linked with UV light. Each membrane was thereafter hybridized with $^{32}$P-end labeled oligonucleotide probes corresponding to wild-type and mutant sequences. After hybridization in 7% polyethylene glycol, 10% SDS, 50 mM sodium phosphate, pH 7.0, for 6 hours, the membranes were washed in 6×SSC, 0.1% SDS with a stringency corresponding to the calculated melting temperature of the probe. Six molecular variants were subjected to such a procedure (variants 3, 5, 7, 9, 10, 15 in Table 2). Variant 14 (L359M) was analyzed by the presence or absence of a PstI site (Kunapuli and Kumar, 1986) in 140 Utah controls and in the 36 more severely hypertensive index cases from Utah.

D. Linkage Disequilibrium Between Marker and Variants of AGT

The haplotype distribution of GT alleles and of the variants observed at residues 174 and 235 were evaluated by maximum likelihood. The M235 allele was in strong linkage disequilibrium with the most common GT allele (16 repeats; GT16) while the M235T variant was found in combination with a wide range of GT alleles. The association between M235 and GT16 was consistent with the greater frequency of GT16 in controls than in hypertensives noted earlier. Because the M235T variant occurred in association with a variety of GT alleles, a greater frequency of M235T in cases would not induce spurious genetic linkage between hypertension and the GT marker.

E. Assay of Angiotensinogen

Plasma angiotensinogen was measured as the generation of angiotensin I after addition of semi-purified human renin to obtain complete cleavage to angiotensin I; the amount of angiotensin I released was measured by radioimmunoassay and angiotensinogen was expressed in ng A-I/ml (Plouin et al., 1989).

EXAMPLE 5

Linkage Analysis Between Renin and Hypertension

The analysis of linkage between renin, the primary candidate, and hypertension was carried out using the methods described in Example 2.

A. RFLP Alleles and Haplotype Frequencies

Similar RFLP frequencies were observed in the 57 hypertensive sib pair probands and the hypertensive reference group was first verified. All RFLPs were in Hardy-Weinberg equilibrium, and similar proportions were found in the two groups. Thus, the same haplotype frequencies were deduced from these three RFLPs with eight possible haplotypes and 70% heterozygosity. The six more frequent haplotypes were observed in the 133 hypertensive siblings.

B. Observed and Expected Concordances According to Each Sibship Size

The 98 hypertensive sib pairs shared 141 ibs alleles (mean ±1 standard deviation=1.44±0.60), while 133.4 (1.36±0.60) were expected under the hypothesis of no linkage, corresponding to a mean excess of 0.08 allele with a 95% confidence interval of −0.04 to +0.20.

According to each sibship size, 63, 49, and 26 alleles were shared by the 41 pairs, 13 trios (39 pairs), and 3 quartets (18 pairs), respectively. The corresponding mean observed Z concordances were 0.77, 1.89, and 4.33. The comparison of the observed and expected concordances, computed in a unilateral t statistic, was not significant (t=0.51, P=0.30).

C. Weights According to the Sibship Sizes

There was a significant excess of ibs allele sharing (13%) when only the 41 sib pairs were considered (63 observed vs. 55.8 expected alleles, t=1.93, P<0.03). However, this was negated by the inclusion of the 13 trios with 4 alleles less than expected, and of the 3 quartets with an excess of only 1.5 alleles.

These variations are reflected by the different levels of the t value according to the different weights that take into account the sibship size. While the t of 0.52 was computed with $w_1=1$, the use of $w_2$ and $w_3$, decreasing the weight given to the large sibships, increased the t statistic although it remained nonsignificant: $t_2=1.34$, P=0.09 and $t_3=1.16$, P=0.12.

D. Discussion

Ninety-eight hypertensive sib pairs from 57 independent sibships were analyzed. The hypertensive sibs were selected if they had a strong predisposition to familial hypertension (at least one parent and one sibling), an early onset of the disease (40.7±12 years), and established essential hypertension. Three different RFLPs located throughout the renin gene (TaqI, HindIII, HinfI) were used as genetic markers. The combination of these three RFLPs allowed the definition of eight haplotypes of which six were observed. The allelic frequencies had been previously determined by the analysis of 102 hypertensive subjects (Soubrier et al. 1990) and were confirmed in the 57 hypertensive sib probands. Taking into account the incomplete heterozygosity of this renin marker (70%) and the absence of parental information in 40 of the 57 sibships, the alleles shared by the affected sibs were considered as identical by state and the appropriate statistical test was used (Lange 1986). No statistically significant difference was found between the observed frequencies of total, half, or null allelic concordances and those expected under the hypothesis of no linkage between the renin gene and hypertension. When the pairs were analyzed independently, these proportions were of 0.50 vs. 0.45, 0.43 vs 0.48, and 0.07 vs 0.07 for the observed vs. expected values, respectively, giving a chi-square (2 df)=1.21, which was not significant. The most appropriate statistic, using the mean number of marker alleles shared by the sibs (Blackwelder and Elston, 1985) and adding the information obtained in each family according to the affected sibship size, did not demonstrate significance (t=0.51, P=0.30), with only a 5.7% excess of i.b.s. renin alleles shared by the 98 hypertensive sib pairs. When the reciprocal of the square root of the variance of the concordance index for each sibship size was used to maximize the power of the test (Motor and Thomson 1985), the t value increased (t=1.31) but remained nonsignificant (P=0.09). Thus, no association was found between renin and hypertension.

EXAMPLE 6

Linkage Analysis Between ACE and Hypertension

The analysis of linkage between ACE and hypertension was carried out using the methods described in Example 3.

A. ACE Growth Hormone Linkage

As sib pair linkage tests depend critically on high heterozygosity at the marker locus (Bishop and Williamson, 1990), cosmids spanning the ACE locus were cloned but failed to identify an informative simple sequence repeat (data not shown). Since the ACE gene has been localized by in situ hybridization to 17q23 (Mattei et al., 1989) a genetically well-characterized chromosomal region (Nakamura et al., 1988), the ACE locus was placed on the genetic map by linkage analysis in 35 CEPH pedigrees using a diallelic polymorphism. (Rigat et al., 1990; Righat et al., 1992). Analysis demonstrated strong linkage to markers fLB17.14, pCMM86 and PM8. Multilocus analysis localized the ACE locus between pCMM86 and PM8 (odds ratio favoring location in this interval=2000:1). The hGH gene, localized by in situ hybridization to the same region (Harper et al., 1982), has also shown strong linkage to these markers (Ptacek et al., 1991). Its sequence (Chen et al., 1989) enabled the development of a highly polymorphic marker based on AAAG and AG repeats lying between the eighteenth and nineteenth Alu repetitive sequences of this locus. The hGH-A1819 marker displayed 24 alleles and heterozygosity of 94.6% in 132 unrelated subjects. A similar hGH marker has been reported to show 82% heterozygosity in 22 unrelated subjects (Polymeropoulos et al., 1991). Pairwise linkage analysis using this marker in 11 CEPH pedigrees demonstrated complete linkage of the hGH and ACE loci in 109 meioses (log of the odds (lod) score=11.68). Multilocus analysis confirmed complete linkage between the ACE and hGH loci with a 95% confidence interval for recombination between these loci of ±0.02. This tight linkage permits use of the hGH marker as a surrogate for the ACE locus in linkage analysis with little or no loss of power.

B. Sib Pair Analysis

The characteristics of hypertensive pedigrees ascertained in Utah have been previously described (see Example 1). All sibs analyzed were diagnosed by hypertensive before 60 years of age (mean 39.3±9.6 yr) and were on antihypertensive medication. Allele frequencies at ACE and hGH loci were compared between 132 controls (Utah grandparents belonging to the CEPH reference families) and 149 hypertensive pedigrees). The frequencies of the two ACE alleles were similar in the two groups (frequencies of the larger allele were 0.455 and 0.448, respectively), as were the frequencies of the 24 alleles at the hGH locus, indicating no linkage disequilibrium between the marker loci and hypertension. From the 149 hypertensive sibships, 237 sib pairs with the hGH marker were genotyped. In the absence of parental genotypes, allele sharing between sibs was scored as 'identity by state' (i.b.s.) (Lang, 1986). The expected number of alleles shared in the total sample under the null hypothesis of no linkage of the marker locus and predisposition to hypertension as 254.8 (1.075 per sib pair); the observed number of alleles shared, 255, coincided with this expectation (t=0.01, ns). The high polymorphism of the hGH marker and the large number of sib pairs studied gives this analysis 80% power to detect a 10.36% excess in the number of alleles shared i.b.s., corresponding to a 12.02 or 13.06% excess of alleles 'identical by descent' (i.b.d.) under a recessive or a dominant model, respectively.

C. Hypertensive Subgroups

The power of such an analysis can be increased by stratifying an aetiologically heterogeneous population into more homogeneous subgroups. Six different subsets of hypertensive pairs were considered sequentially. As a possible enrichment of the genetic component determining high blood pressure, two subsets were selected: (1) 52 pairs in which both sibs had early onset of hypertension (prior to 40 years of age); (2) 31 sib pairs with more severe hypertension, in whom two or more medications were required for blood pressure control. No excess allele sharing was observed in either group. As a control for the potential influence of obesity, a significant confounding factor, we separately analyzed the 71 lean hypertensive pairs in which both sibs had a body mass index less than 20 kg m$^{-2}$ (mean 25.9±2.8 kg m$^{-2}$). Again, allele sharing did not depart from that expected under random segregation of the marker and hypertension.

It is of further interest to stratify for intermediate phenotypes which could be related to either the ACE or hGH loci. ACE plasma concentration shows evidence for a major gene effect but no relation to blood pressure in healthy subjects (Righat et al., 1990; Alhenc-Gelas et al., 1991). Chronic elevations of hGH can induce not only increased lean body mass and hypertension but also insulin resistance (Bratusch-Marrain et al., 1982), a common feature in both human hypertension (Ferrannini et al., 1987; Pollare et al., 1990) and SHR (Reaven et al., 1991). Sib pairs with (a) high lean body mass, (b) high fasting insulin levels and (c) high fasting insulin levels after adjustment for body mass, since body mass is strongly correlated with insulin levels ($r=0.40$, $p<0.001$ in this study) were stratified. Again, no departure from random expectation was observed in any subgroup.

D. Discussion

These results demonstrate an absence of linkage between the ACE/hGH loci and hypertension in this population. This study had substantial power to detect linkage, analyzing a large number of hypertensive sib pairs and using an extremely polymorphic marker that displays no recombination with ACE. The lack of departure from random segregation of the marker locus and hypertension, together with the absence of linkage disequilibrium between ACE and hGH markers and hypertension, exclude the hypothesis that common variants at this locus could have a significant effect on blood pressure. The analyses of more homogeneous subsets of hypertensive pairs potentially enriched for a genetic component were also negative, though the 95% confidence limits on those subject remain large. These results do not rule out the possibility that rare mutation of the ACE gene could, like LDL-receptor mutations in hypercholesterolemia (Goldstein and Brown, 1979), have a significant effect on the trait but account for only a small percentage of affected individuals in the population. Thus, no association was found between ACE and hypertension.

EXAMPLE 7

Linkage Analysis Between AGT and Hypertension

The analysis of linkage between AGT and hypertension was carried out using the methods described in Example 4. Three distinct steps were utilized in the analytical approach to identify and confirm a linkage between the AGT gene and hypertension: (1) a genetic linkage study; (2) an identification of molecular variants of AGT followed by a comparison of their frequencies in hypertensive cases and controls; and (3) an analysis of variance of plasma angiotensinogen concentration in hypertensive subjects as a function of AGT genotypes.

When parental alleles at a marker locus can be identified unambiguously in their offspring, the observed proportion of sibling pairs sharing 0, 1 or 2 alleles identical by descent (i.b.d.) can be directly compared to the expected proportions of ¼, ½, and ¼ under the hypothesis of no genetic linkage. For a disease of late onset, however, parents are usually not available for sampling. Furthermore, even for a marker with multiple alleles and high heterozygosity, the identity by state (i.b.s.) of two alleles in a pair of siblings does not imply that they are identical by descent, that is, inherited from the same parental gene: this allele may have been present in more than one of the four parental genes. In such cases, one must express the probability that two alleles in the off-spring be identical by state as a function of mendelian transmission rules and allelic frequencies in the reference population. The mean number of alleles shared by siblings is then compared to the value expected under the assumption of independent segregation of hypertension and marker through a one-sided Student t-test (Blackwelder and Elston, 1985; Lange, 1986).

After molecular variants of AGT were identified, their frequencies in cases and controls were directly compared. The subject in each hypertensive sibship with lowest identification number was selected as the index case; the panel of control subjects consisted of a sample of healthy, unrelated individuals from the same population.

Lastly, the effect of AGT genotypes on plasma angiotensinogen was tested by analysis of variance of all hypertensive subjects for which a measurement was available, taking into account gender or population of origin as an independent, fixed effect.

A. Genetic Linkage Between AGT and Essential Hypertension

A total of 215 sibships were collected at two centers under separate sampling procedures. The Salt Lake City sample consisted of 132 sibships, each with at least two hypertensive siblings on antihypertensive medication, which had been ascertained directly from the local population. In Paris, patients from 83 families had been selected in a hypertension clinic on the basis of strict criteria with respect to blood pressure and body-mass index. The impact of the difference in ascertainment protocols is reflected in the summary statistics presented in Table 3. A highly informative genetic marker at the AGT locus, based on a variable tandem repeat of the sequence motif 'GT' (Kotelevstev et al., 1991), was characterized in all study subjects; reference frequencies and genotypes (FIG. 1) were determined. Because of the anticipated etiological heterogeneity of this disease, analyses were performed not only on total samples, but also on pre-defined subsets of the data which had the potential of exhibiting greater genetic homogeneity, such as subjects with earlier onset or with more severe hypertension (Jeunemaitre et al., 1992). Linkage did not reach significance in the total sample from Salt Lake City ($t=1.22$, $p=0.11$). However, a 7.7% excess of alleles shared by hypertensive siblings was observed in the total sample from Paris ($t=1.71$, $p<0.05$), and a slightly greater level of significance was achieved when both samples were pooled ($t=2.02$, $p=0.02$, Table 4). Similar results were observed when only subjects with earlier onset of hypertension were considered (Table 5). By contrast, a more significant, 15% to 18% excess of alleles shared by the sibling pairs was observed when analysis was restricted to patients with "more severe" hypertension, predefined in both groups as subjects requiring two medications for blood pressure control or with diastolic blood pressure equal to or greater than 100 mmHg (Table 5). In addition to the greater significance achieved by pooling the "more severe" hypertensive pairs from both studies ($t=3.40$, $p<0.001$), the replication of this finding in two different hypertensive populations is of critical relevance in evaluating this statistical evidence.

TABLE 4

Sib Pair Linkage Analysis at the Angiotensinogen Locus in Salt Lake City and Paris

| Study | Sibships n | Pairs n | Alleles Shared Observed/ Expected | Significance Excess | t | p |
|---|---|---|---|---|---|---|
| Salt Lake City | | | | | | |
| Pairs | 102 | 102 | 132/126.9 | | | |

TABLE 4-continued

Sib Pair Linkage Analysis at the Angiotensinogen Locus in Salt Lake City and Paris

| Study | Sibships n | Pairs n | Alleles Shared Observed/ Expected | Significance Excess | t | p |
|---|---|---|---|---|---|---|
| Trios | 20 | 60 | 85/74.7 | | | |
| Quartets | 7 | 42 | 56/52.3 | | | |
| Quintet | 1 | 10 | 8/12.4 | | | |
| Sextets | 2 | 32 | 31/37.3 | | | |
| TOTAL | 132 | 244 | 312/303.6 | 3.8% | 1.22 | 0.11 |
| Paris | | | | | | |
| Pairs | 62 | 62 | 86/74.4 | | | |
| Trios | 19 | 57 | 71/70.7 | | | |
| Quartet | 1 | 6 | 9/7.5 | | | |
| Quintet | 1 | 10 | 8/10 | | | |
| TOTAL | 83 | 136 | 175/162.6 | 7.7% | 1.71 | <.05 |
| TOTAL | 215 | 379 | 487/466.2 | 5.1% | 2.02 | 0.02 |

For each sample the following is reported; the number of sibships and sibling pairs analyzed, the observed and expected number of alleles shared by the siblings for each sibship size and the excess of alleles shared (%) after weighting by sibship size.

TABLE 5

Genetic Linkage in Sib Pairs Selected for Early Onset or More Severe Hypertension

| | Pairs n | Alleles Shared (observed/expected) | Excess | t | p |
|---|---|---|---|---|---|
| Age Dx < 45 years | | | | | |
| Salt Lake City | 110 | 143/136.9 | 7.1% | 1.51 | p = 0.07 |
| Paris | 61 | 80/71.6 | 11.6% | 1.68 | p = 0.05 |
| TOTAL | 171 | 223/208.5 | 8.6% | 2.23 | p < 0.02 |
| Rx ≧ 2 drugs or DBP ≧ 100 mmHg | | | | | |
| Salt Lake City | 50 | 74/62.3 | 18.0% | 2.58 | p < 0.01 |
| Paris | 60 | 85/72.9 | 15.3% | 2.25 | p < 0.02 |
| TOTAL | 110 | 159/136.2 | 17.1% | 3.40 | p < 0.001 |

Because estrogens stimulate angiotensinogen production (Cain et al., 1971; Ménard and Catt, 1973), the data were partitioned by gender (Table 6). In the Salt Lake City as well as in the Paris samples, linkage remained significant among male-male pairs only (t=2.42, p<0.01, samples pooled). Furthermore, the 37 male-male pairs from both samples who also met the criteria for 'more severe' hypertension exhibited a 33% excess of shared alleles (t=3.60, p<0.001).

Forty-eight women in the Salt Lake City sample were taking synthetic estrogens or oral preparations containing natural estrogens, while none in the Paris sample were doing so; still, there was no excess of shared alleles among the 35 Utah female pairs who were not taking exogenous estrogens.

TABLE 6

Genetic Linkage in Hypertensive Sib Pairs of Same Gender

| | Pairs n | Alleles Shared (observed/expected) | Excess | t | p |
|---|---|---|---|---|---|
| Male-Male Pairs | | | | | |
| Salt Lake City | 60 | 81/74.6 | 11.0% | 1.70 p < 0.05 | |
| Paris | 37 | 52/44.4 | 15.4% | 1.76 p < 0.05 | |
| TOTAL | 97 | 133/118.0 | 12.7% | 2.42 p < 0.01 | |
| Female-Female Pairs | | | | | |
| Salt Lake City | 79 | 96/98.3 | −2.3% | <0 | |
| Paris | 36 | 45/43.7 | 1.4% | 0.31 p = 0.38 | |
| TOTAL | 115 | 139/142.0 | −1.2% | <0 | |

B. Association Between Hypertension and Molecular Variants of AGT

Figure 3:
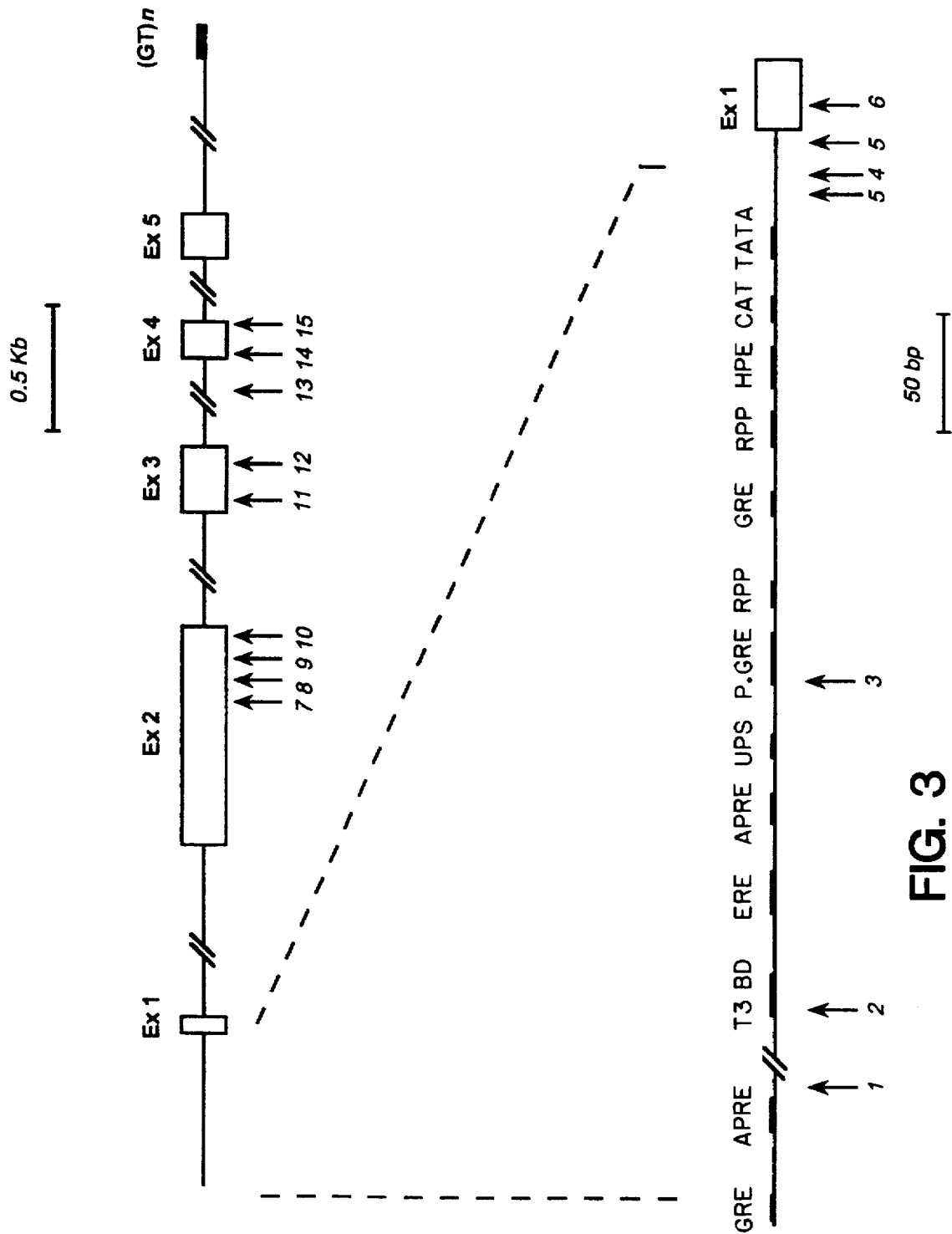
FIG. 3. Map of the human genomic angiotensinogen gene and location of identified variants. Exons of the angiotensinogen gene are represented by open boxes at the top of the figure. An expanded view of the 5' flanking region of the gene is shown below, with the location of transcriptional regulatory sequences indicated by filled boxes: CAT, TATA and RNA polymerase III (RPP) promoter elements; hormone responsive elements for glucocorticoid (GRE, P.GRE: putative GRE), estrogen (ERE), or thyroid hormone (TRE); hepatic specific element (HSE); acute phase response element (APRE); putative enhancer element (ENH). The locations of sequence variants identified in hypertensive subjects are indicated by numbered arrows; exact location and nature of each variant is indicated in Table 2 below.

The observation of significant genetic linkage between essential hypertension and a marker at the AGT locus suggested that molecular variants in this gene might be causally implicated in the pathogenesis of essential hypertension. A direct search for such variants in all exons and in a 682-bp segment of the 5' noncoding region of AGT was performed on a sample consisting of the index cases of the more severely hypertensive pairs from both populations. Variants detected by electrophoresis of enzymatically amplified DNA segments under nondenaturing conditions (Orita, 1989) were submitted to direct DNA sequencing (Hata et al., 1990) (FIG. 2). At least 15 distinct molecular variants have been identified, including five nucleotide substitutions in the 5' region of the gene, and ten silent and missense variants (FIG. 3, Table 2). No variants have been detected within the N-terminal portion of exon 2 that encodes the site cleaved by renin.

The prevalence of each identified variant was compared between hypertensive index cases and control subjects. For the Salt Lake City sample, the first variant detected, M235T (a change from methionine to threonine at amino acid 235 of AGT), was significantly more frequent in all hypertensive index cases than in controls, with a further increase in frequency among the more severely affected index cases (Table 7). These results were replicated in the Paris sample. The association was significant in either sex. In particular, M235T was significantly more prevalent among female hypertensives (0.51) than in controls (0.37) ($\chi^2_1=16.9$, p<0.001).

TABLE 7

Linkage Disequilibrium Between Controls and Hypertensives

| | | T174M | | M235T | |
|---|---|---|---|---|---|
| | n | q | $X_1^2$ | q | $X_1^2$ |
| Salt Lake City | | | | | |
| Controls | 280 | .08 | | .35 | |

TABLE 7-continued

Linkage Disequilibrium Between Controls and Hypertensives

|  | | T174M | | M235T | |
|---|---|---|---|---|---|
|  | n | q | $X_1^2$ | q | $X_1^2$ |
| All Probands | 264 | .12 | 2.8,ns | .44 | 4.5, p < 0.05 |
| More Severe Probands | 72 | .19 | 8.4, p < 0.01 | .49 | 4.5, p < 0.05 |
| Paris | | | | | |
| Controls | 184 | .09 | | .38 | |
| All Probands | 166 | .18 | 5.9, p < 0.02 | .52 | 6.7, p < 0.01 |
| More Severe Probands | 88 | .19 | 5.5, p < 0.02 | .52 | 4.2, p < 0.05 |
| Total | | | | | |
| Controls | 464 | .09 | | .36 | |
| All Probands | 430 | .14 | 5.3, p < 0.05 | .47 | 11.1, p < 0.001 |
| (males/females) | (224/206) | (.16/.13) | | (.44/.51) | |
| More Severe Probands | 160 | .17 | 7.4, p < 0.01 | .51 | 11.6, p < 0.001 |
| (males/females) | (96/64) | (.14/.21) | | (.45/.59) | |

In each group, are indicated the number of alleles analyzed (n), the allele frequency (q), and the significance of the association between controls and hypertensives calculated with a Chi square 1 d.f. All probands refers to the index hypertensive subjects of each sibship (n = 132, Salt Lake City; n = 83, Paris); more severe probands refers to the index subjects of the more severely affected pairs. There was no significant difference in M235T and T174M allelic frequencies between males and females. No departure from Hardy-Weinberg equilibrium was observed in repartition of these genotypes.

Of the other variants tested, only T174M also displayed significant association in both samples (Table 7). Analysis of the distribution of M235T and T174M genotypes indicates that these two variants were in complete linkage disequilibrium ($\chi^2_4$=36.4, p<0.0001): T174M was present in a subset of chromosomes carrying the M235T allele. When the frequencies of these haplotypes were contrasted among hypertensives and control subjects, haplotypes carrying M235T, with or without T174M, were observed more often among all hypertensive index cases (0.14 and 0.33, n=215) than in controls (0.09 and 0.28, n=232), both differences being significant ($\chi^2_1$=5.6, p<0.02 and $\chi^{21}$=13.5, p<0.01).

C. Association with Plasma Concentrations of Angiotensinogen

A possible relationship between plasma concentrations of angiotensinogen and two molecular variants of this protein (M235T and T174M) was tested by analysis of variance, as a function of genotype and gender, in hypertensive subjects in each sample. Women taking oral preparations of estrogens were excluded from this analysis. No significant differences were observed when subjects were classified according to genotype at residue 174. By contrast, plasma concentrations of angiotensinogen were significantly higher in women carrying the M235T variant in each population sample; when both samples were jointly considered in an analysis of variance taking into account gender and population as fixed effects, genotypic differences were highly significant ($F_{2, 313}$=14.9, p<0.0001) (Table 8).

TABLE 8

Influence of the M2325T Variant on Plasma Angiotensinogen Concentrations

| M235T | AA | Aa | aa | Significance: F,p |
|---|---|---|---|---|
| Salt Lake City | 1422 ± 247 (67) | 1479 ± 311 (109) | 1641 ± 407 (33) | 5.92, p < 0.005[1] |
| Males | 1376 ± 247 (42) | 1404 ± 265 (59) | 1499 ± 207 (18) | 1.53, ns |
| Females | 1500 ± 232 (25) | 1566 ± 340 (50) | 1811 ± 519 (15)[2,3] | 3.91, p < 0.02 |
| Paris | 1085 ± 210 (32) | 1318 ± 383 (55) | 1514 ± 511 (29) | 7.90, p < 0.001[1] |
| Males | 1086 ± 244 (17) | 1311 ± 290 (26)[4] | 1377 ± 606 (10)[2] | 2.82, p = 0.07 |
| Females | 1084 ± 173 (15) | 1324 ± 456 (29)[4] | 1586 ± 455 (19)[2,3] | 6.44, p < 0.01 |
| Total | 1313 ± 283 (99) | 1425 ± 344 (164) | 1582 ± 459 (62) | 14.90, p < 0.0001[5] |
| Males | 1293 ± 277 (59) | 1375 ± 274 (85) | 1456 ± 391 (28)[2] | 3.10, p < 0.05 |
| Females | 1344 ± 292 (40) | 1477 ± 401 (79) | 1685 ± 490 (34)[2,3] | 6.82, p < 0.001 |

Plasma angiotensinogen concentrations are expressed as mean ± 1 S.D. (ng/ml). A: allele M235; a: allele 235T. The statistical significance is tested by: (1) one-way analysis of variance; (2) two-way analysis of variance with gender as a fixed effect[1]; and (3) three-way analysis of variance with gender and population as fixed effects.[5]
[2]p < 0.05 between heterozygotes and homozygotes M235.
[3]p < 0.05 between homozygotes M235T and homozygotes M235.
[4]p < 0.05 between homozygotes M235T and heterozygotes.

The effect associated with M235T appeared to be codominant in females. Higher concentrations were found in females than males in Salt Lake City (t=4.3, p<0.001) but not in Paris (t=1.41, p=0.16). While the effect of estrogens on angiotensinogen production may account for the gender difference noted in Salt Lake City, a difference in mean values between the two samples is less likely to be of physiological significance; all subjects belonging to a given population sample were assayed concurrently and referred to the same standard, but measurements for Salt Lake City and Paris samples were performed 6 months apart, using different preparations of renin and different standards.

D. Analysis of the G-6A Variant

The data detailed above contained insufficient evidence concerning the G-6A variant which led to the interpretation that the G-6A variant occurred only in total association with A-20C variant. Thus, in Table 2, it was reported that the frquency of the genes carrying both A-20C and G-6A variants was 14% in Utah Controls (C) and 19% in Utah Hypertensives (H). The frequency was 18% in French hypertensives, with no testing performed in French controls. The frequency of the M235T variant was 36% and 38% in Utah and French controls, respectively. While this data is correct, it did not take into consideration the fact that the G-6A variant could also occur on genes which did not carry the A-20C variant.

Studies were conducted in Japanese and Utah populations and analyzed as described above. In tests involving 107 random Caucasian controls from Utah and 99 random Japanese individuals, the G-6A variant was seen in over 90% of the Caucasian genes carrying M235T and in 98% of the corresponding Japanese genes. The G-6A variant was seen in only one Caucasian gene carrying the native M235 gene. See Table 9. Thus, more than 90% of the Utah hypertensives carrying M235T also carry G-6A, rather than the 40% suggested in Table 2.

TABLE 9

Frequencies of AGT Haplotypes in Caucasian and Japanese Controls

| Haplotype | Caucasians | Japanese |
|---|---|---|
| M235[1], G(-6)[1] | 0.607 | 0.242 |
| M235, A(-6) | 0.005 | 0.000 |
| T235, G(-6) | 0.038 | 0.015 |
| T235, A(-6) | 0.350 | 0.743 |
| Total | 1.000 | 1.000 |

[1]The wild-type sequence at these positions.

Discussion

Three sets of observations—genetic linkage, allelic associations, and differences in plasma angiotensinogen concentrations among AGT genotypes—in two independent samples of hypertensive subjects establishes involvement of angiotensinogen in the pathogenesis of essential hypertension.

1. Genetic Linkage in Hypertensive Siblings

Genetic linkage was inferred through the application of first principles of Mendelian genetics to pairs of related individuals (Blackwelder and Elston, 1985), an approach requiring a large number of affected pairs and a highly polymorphic marker at the test locus (Risch, 1990; Bishop and Williamson, 1990). This study design is well suited to common disorders where the anticipated multiplicity and heterogeneity of causal factors defies conventional approaches that rely on explicit formulation of a model of inheritance.

In the Utah sample, significant linkage was achieved only for the subset of more severely affected subjects—as defined by the use of two antihypertensive drugs or by a diastolic blood pressure equal to or greater than 100 mmHg; by contrast, linkage reached significance in the total sample in Paris. This observation most likely reflects the different ascertainment schemes applied in each study. Salt Lake City sibships represent a population-based collection of hypertensive subjects, whereas subjects in Paris were recruited through referral to a hypertension clinic and with the application of strict exclusion criteria (see Example 1). The former sample has the merit of being population-based; however, the inclusion of less severely affected subjects, as reflected by lower treated blood pressure values than in the French sample, may have led to the appearance of greater etiological heterogeneity in the total sample.

2. Association Between Hypertension and Molecular Variants of AGT

Genetic linkage indicated that variants of AGT could be involved in the pathogenesis of essential hypertension. Among the 15 molecular variants of the AGT gene identified, significant association with hypertension was observed for two distinct amino acid substitutions, M235T and T174M. The significance of this association was established by contrasting allelic frequencies in hypertensive and control subjects. Although this design is liable to biases due to uncontrolled stratification, three arguments support the interpretation that the observed associations are not spurious: (1) significance is obtained in independent samples from two different populations; (2) gene frequencies are remarkably similar in these two samples, suggesting that little variation should be anticipated among Caucasians of Northern and Western European descent; (3) no differences in allelic frequencies among these hypertensive and control groups have been observed at other loci including renin, angiotensin converting enzyme and HLA (Examples 5 and 6).

Variants M235T and T174M exhibited complete linkage disequilibrium, as T174M occurred on a subset of the haplotypes carrying the M235T variant, and both haplotypes were observed at higher frequency among hypertensives. Several interpretations can be proposed to account for this observation: (1) M235T directly mediates a predisposition to hypertension; (2) an unidentified risk factor is common to both haplotypes; (3) each haplotype harbors a distinct risk factor.

Although both variants were found significantly more often in female hypertensives than in control subjects, no linkage was evident among pairs of female hypertensives in either sample. These observations could be reconciled by postulating that angiotensinogen contributes to hypertensive risk directly in males but indirectly in females, where another estrogen-modulated factor may mediate the impact of the angiotensinogen-associated predisposition; documented differences in the effects of testosterone and estrogens on the regulation of genes of the renin-angiotensin system support this hypothesis (Bachmann et al., 1991). While it is conceivable that the predispositions identified by linkage and by association represent independent variants, the parallel increase of both association and linkage in subsets of the data suggests that they are two manifestations of the same genetic determinant.

In addition to the significant association with hypertension initially noted for M235T and T174M variants, analysis of the G-6A variant shows this variant is also significantly associated with hypertension. The very strong association observed between M235T and G-6A has two important implications: (1) all associations noted between M235T and hypertension extend directly to G-6A, that is, G-6A is also diagnostic of a predisposition to hypertension; (2) it is unlikely that statistical tests alone can resolve the relative merit of either one as a marker for this predisposition, as it would require much greater sample sizes than those analyzed so far. These new observations now dictate four alternative interpretations of the data (instead of the former two): (1) M235T and G-6A both serve as markers for a predisposition to the development of hypertension encoded by yet another, unknown molecular variant; (2) M235T is causally involved while G-6A is a passive "hitchhiker"; (3) G-6A is causally involved, M235T being the passive "hitchhiker"; or (4) both M235T and G-6A are causal; each contributes a difference in the function of the angiotensinogen gene and protein. Regardless of which interpretation may be correct, the data clearly demonstrates the significant association of each variant with hypertension and the ability of both two variants to be an indicator of predisposition to hypertension.

In view of these findings, molecular variants of the angiotensinogen gene constitute an inherited predisposition to essential hypertension in humans.

EXAMPLE 8

Screening for AGT Variants

Healthy subjects and pregnant women were screened for the M235T variant using PCR amplification and allele-specific oligonucleotide hybridization as described in Example 4. It was found that healthy subjects who carried the M235T variant had plasma levels of angiotensinogen higher than in non-carriers, and also had higher blood pressure. Both of these differences were found to be statistically significant. It was also found that the variant was not limited to Caucasians. The M235T variant was found to be significantly increased in women presenting preeclampsia during pregnancy.

While the invention has been disclosed in this patent application by reference to the details of preferred embodiments of the invention, it is to be understood that the disclosure is intended in an illustrative rather than in a limiting sense, as it is contemplated that modifications will readily occur to those skilled in the art, within the spirit of the invention and the scope of the appended claims.

LIST OF REFERENCES

Arnal, J. F., et al. (1991). *Am. J. Med.* 90:17–22.
Alhenc-Gelas, F., et al. (1991). *J. Lab. Clin. Med.* 117:33–39.
Bachmann, J., et al. (1991). *J. Steroid Biochem. Mol. Biol* 40:511–515.
Blackwelder, W. C. and Elston, R. C. (1985). *Genet. Epidemiol.* 2:85–97.
Bishop, D. T. and Williamson, J. A. (1990). *Am. J. Hum. Genet.* 46:254–265.
Bratusch-Marrain, P. R. et al. (1982). *J. Clin. Endocrinol. Met.* 55:973–982.
Brown, A. J., et al. (1981). *Am. J. Physiol.* 241:H381–H388.
Cain, M. D., et al. (1976). *J. Clin. Endocrinol.* 33:671–676.
Campbell, D. J., and Habener, J. F. (1986). *J. Clin. Invest.* 78:1427–1431.
Carrell, R. W., and Boswell, D. R. (1986). In *Pro-teinase Inhibitors*, Barrett and Salvesen, eds., (Elsevier Science Publishers BV, Biomedical Division), pp. 403–420.
Cariello (1988). *Human Genetics* 42:726.
Chen, E. Y., et al. (1989). *Genomics* 4:479–487.
Clauser, E., et al. (1989). *Am. J. Hypertens.* 2:403–410.
Conner, B. J., et al. (1983). *Proc. Nat. Acad. Sci. USA.* 80:278–282.
Corvol, P., et al. (1989). *Clin. Exper. Hypertension: Theory & Practice.* A11:1053–1073.
Cotton, et al. (1988). *Proc. Nat. Acad. Sci. USA* 85:4397.
Cudworth, A. G., and Woodrow, J. C. (1975). *Brit. Med. J. III:* 133–135.
Dausset, J., et al. (1990). *Genomics* 6:575–577.
Deng, Y., and Rapp, J. P. (1992). *Nature Genetics* 1:267–272.
Fasola, A. F., et al. (1968). *J. Appl. Physiol.* 25:410–415.
Ferrannini, E., et al. (1987). *N. Eng. J. Med.* 317:350–357.
Finkelstein, J., et al. (1990). *Genomics* 7:167–172.
Froguel, P., et al. (1992). (1992). *Nature* 356:162–164.
Froussard, P. M., et al. (1986a). *Nucl. Acids Res.* 14:6778.
Froussard, P. M., et al. (1986b). *Nucl. Acids Res.* 14:4380.
Fukamizu, A., et al. (1989). *J. Biol. Chem.* 265:7576–7582.
Gaillard, I., et al. (1989). *DNA* 8:87–99.
Gardes, J., et al. (1982). *Hypertension* 4:185–189.
Gould, A. B., et al. (1971). *Cardiovasc. Res.* 5:86–89.
Hall, J. E., and Guyton, A. C. (1990). In *Hypertension: Pathophysiology Diagnosis and Management*, Laragh, J. H. and Brenner, B. M., eds., (Raven Press, Ltd., New-York), pp. 1105–1129.
Hamilton, M., et al. (1954). *Clin. Sci.* 13:273–304.
Harper, M. E., et al. (1982). *Am. J. Hum. Genet.* 34:227–234.
Harrop, S. H., et al. (1990). *Hypertension* 16:603–614.
Hata, A., et al. (1990). *Nucl. Acids Res.* 18:5407–5411.
Hilbert, P., et al. (1991). *Nature* 353:521–528.
Hill, W. G. (1975). *Biometrics* 31:881–888.
Hodge, S. E. (1984). *Genet. Epidemiol.* 1:109–122.
Jacob, H. J., et al. (1991). *Cell* 67:213–224.
Jeunemaitre, X., et al. (1992a). *Nature Genetics* 1:72–75.
Jeunemaitre, X., et al. (1992b). *Hum. Genet.* 88:301–306.
Joint National Committee on Detection, Evaluation and Treatment of Hypertension (1985). Final report of the Subcommittee on Definition and Prevalence. *Hypertension* 7:457–468.
Kimura, S., et al. (1992). *EMBO J.* 11:821–827.
Kinszler, K. W., et al. (1991). *Science* 251:1366–1370.
Kotelevtsev, Y. V., et al. (1991). *Nucl. Acids Res.* 19:6978.
Kunapuli, S. P., and Kumar, A. (1986). *Nucl. Acids Res.* 14:7509.
Kurtz, T. W., et al. (1990). *J. Clin. Invest.* 85:1328–1332.
Lalouel, J. M. (1990). In *Drugs Affecting Lipid Metabolism*, A. M. Gotto and L. C. Smith, eds. (Elsevier Science Publishers, Amsterdam), pp. 11–21.
Lander, E. S., and Botstein, D. (1986). *Cold Spring Harbor Symp. Quant. Biol.* 51:46–61.
Lander, E. S., and Botstein, D. (1989). *Genetics* 121:185–199.
Lange, K. (1986). *Am. J. Hum. Genet.* 50:283–290.
Lathrop, G. M., and Lalouel, J. M. (1991). In *Handbook of Statistics*, Vol. 8 (Elsevier Science Publishers, Amsterdam), pp. 81–123.
Lathrop, G. M., et al. (1984). *Proc. Nat. Acad. Sci. USA* 81:8443–3446.
Lifton, R. P., et al. (1992). *Nature* 355:262–265.
Masharani, U. (1989). *Nucl. Acids Res.* 17:467
Mattei, M. G., et al. (1989) *Cytogenet. Cell Genet.* 51:1041.
Menard, J., and Catt, K. J. (1973). *Endocrinology* 92:1382–1388.
Menard, J., et al. (1991). *Hypertension* 18:705–706.
Modrich, P. (1991). *Ann. Rev. Genet.* 25:229–253.
Motro, U. and Thomson, G. (1985). *Genetics* 110:525–538.

Mullins, J. J., et al. (1990). *Nature* 34:541–544.
Nakamura, Y. et al. (1988). *Genomics* 2:302–309.
Noftilan, A. J., et al. (1989). *Hypertension* 14:614–618.
Novack, et al. (1986). *Proc. Nat. Acad. Sci USA* 83:586.
Ohkubo, H., et al. (1990). *Proc. Nat. Acad. Sci. USA* 87:5153–5157.
Orita, M., et al. (1989). *Proc. Nat. Acad. Sci. USA* 86:2766–2770.
Plouin, P. F., et al. (1989). *Presse Med.* 18:917–921.
Pollare, T. et al. (1990). *Metabolism* 39:167–174.
Polymeropoulous, M. H., et al. (1991). *Nucl. Acids Res.* 19:689.
Pratt, R. E., et al. (1989). *Am. J. Physiol.* 256:F469–F474.
Ptacek, L. J., et al. (1991). *Am. J. Hum. Genet.* 49:378–382.
Rano & Kidd (1989). *Nucl. Acids Res.* 17:8392.
Rapp, J. P., et al. (1989). *Science* 243:542–544.
Reaven, G. M. and Cheng, H. (1991). *Am. J. Hypertens.* 4:34–38.
Riget, B., et al. (1990). *J. Clin. Invest.* 86:1343–1346.
Riget, B., et al. (1992). *Nucl. Acids Res.* in press.
Risch, N. (1990). *Am. J. Hum. Genet.* 46:242–253.
Sassaho, P., et al. (1987). *Am. J. Med.* 83:227–235.
Sealey, J. E., and Laragh, J. H. (1990). In *Hypertension: Pathophysiology, Diagnosis and Management,* J. H. Laragh and B. M. Brenner, eds. (Raven Press, New York), pp. 1287–1317.
Sheffield, V. C., et al. (1989). *Proc. Nat. Acad. Sci. USA* 86: 232–236.
Shenk, et al. (1975). *Proc. Nat. Acad. Sci. USA* 72:989.
Soubrier, F., et al. (1986). *Gene* 41:85–92.
Soubrier, F. (1990). *Hypertension* 16:712–717.
Suarez, B. K., et al. (1978). *Ann. Hum. Genet.* 42:87–94.
Suarez, B. K. et al. (1983). *Ann. Hum. Genet.* 47:153–159.
Suarez, B. K., and Van Eerdewegh, P. (1984). *Am. J. Med. Genet.* 18:135–146.
Tewksbury, D. A. (1990). In *Hypertension: Pathophysiology, Diagnosis and Management,* Laragh, J. H. and Brenner, B. M., eds., (Raven Press, Ltd., New York), pp. 1197–1216.
Walker, W. G., et al. (1979). *Hypertension* 1:287–291.
Ward, R. (1990). In *Hypertension: Pathophysiology, Diagnosis and Management,* Laragh, J. H. and Brenner, B. M., eds., (Raven Press, Ltd., New York), pp. 81–100.
Watt, G. C. M., et al. (1992). *J. Hypertens.* 10:473–482.
White, R. L., and Lalouel, J. M. (1987). In *Advances in Human Genetics,* Vol. 16, H. Harris and K. Hirschhorn, eds. (Plenum Press, New York), pp. 121–228.
Williams, R. R., et al. (1988). *J. Am. Med. Assn.* 259:3579–3586.
Williams, R. R. (1989). *Hypertension* 14:610–613.
Yongue, B. G., et al. (1991). *Hypertension* 17:485–491.

---

What is claimed is:

1. A method for determining the predisposition of a human to essential hypertension or pregnancy induced hypertension which comprises analyzing the DNA sequence of the angiotensinogen (AGT) gene of said human for the mutation G-6A, whereby the presence of said mutation is indicative of a predisposition of said human to essential hypertension or pregnancy induced hypertension.

2. The method of claim 1 wherein the genomic sequence of the AGT gene of said human is analyzed.

3. The method of claim 1 wherein the cDNA sequence of the AGT gene of said human is analyzed.

4. The method of claim 1 wherein a part of the genomic sequence of the AGT gene of said human is analyzed.

5. The method of claim 1 wherein a part of the cDNA sequence of the AGT gene of said human is analyzed.

6. The method of claim 1 wherein said analysis is carried out by hybridization.

7. The method of claim 6 wherein said hybridization is with an allele-specific oligonucleotide probe.

8. The method of claim 1 wherein said analysis is carried out by sequence analysis.

9. The method of claim 1 wherein said analysis is carried out by SSCP analysis.

* * * * *

SEQUENCE LISTING ( 1 ) GENERAL INFORMATION:

( i i i ) NUMBER OF SEQUENCES: 22

( 2 ) INFORMATION FOR SEQ ID NO:1:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:1:

ACCATTTGCA ATTGTACAG C        21

( 2 ) INFORMATION FOR SEQ ID NO:2:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:2:

GCCCGCTCAT GGGATGTG

18

( 2 ) INFORMATION FOR SEQ ID NO:3:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:3:

AAGACTCTCC CCTGCCCCTC T

21

( 2 ) INFORMATION FOR SEQ ID NO:4:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:4:

GAAGTCTTAG TGATCGATGC AG

22

( 2 ) INFORMATION FOR SEQ ID NO:5:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:5:

AGAGGTCCCA GCGTGAGTGT

20

( 2 ) INFORMATION FOR SEQ ID NO:6:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Homo sapiens ( x i ) SEQUENCE DESCRIPTION: SEQ ID NO:6:

AGACCAGAAG GAGCTGAGGG     20

( 2 ) INFORMATION FOR SEQ ID NO:7:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:7:

GTTAATAACC ACCTTTCACC CTT     23

( 2 ) INFORMATION FOR SEQ ID NO:8:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:8:

GCAGGTATGA AGGTGGGGTC     20

( 2 ) INFORMATION FOR SEQ ID NO:9:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:9:

AGGCCAATGC CGGGAAGCCC     20

( 2 ) INFORMATION FOR SEQ ID NO:10:

( i ) SEQUENCE CHARACTERISTICS:
  ( A ) LENGTH: 20 base pairs
  ( B ) TYPE: nucleic acid
  ( C ) STRANDEDNESS: single
  ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
  ( A ) ORGANISM: Homo sapiens ( x i ) SEQUENCE DESCRIPTION: SEQ ID NO:10:

ATCAGCCCTG CCCTGGGCCA  20

( 2 ) INFORMATION FOR SEQ ID NO:11:

( i ) SEQUENCE CHARACTERISTICS:
  ( A ) LENGTH: 20 base pairs
  ( B ) TYPE: nucleic acid
  ( C ) STRANDEDNESS: single
  ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
  ( A ) ORGANISM: Homo sapiens ( x i ) SEQUENCE DESCRIPTION: SEQ ID NO:11:

GATGCGCACA AGGTCCTGTC  20

( 2 ) INFORMATION FOR SEQ ID NO:12:

( i ) SEQUENCE CHARACTERISTICS:
  ( A ) LENGTH: 20 base pairs
  ( B ) TYPE: nucleic acid
  ( C ) STRANDEDNESS: single
  ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
  ( A ) ORGANISM: Homo sapiens ( x i ) SEQUENCE DESCRIPTION: SEQ ID NO:12:

GCCAGCAGAG AGGTTTGCCT  20

( 2 ) INFORMATION FOR SEQ ID NO:13:

( i ) SEQUENCE CHARACTERISTICS:
  ( A ) LENGTH: 20 base pairs
  ( B ) TYPE: nucleic acid
  ( C ) STRANDEDNESS: single
  ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:

(A) ORGANISM: Homo sapiens (xi) SEQUENCE DESCRIPTION: SEQ ID NO:13:

TCCCTCCCTG TCTCCTGTCT                    20

(2) INFORMATION FOR SEQ ID NO:14:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (xi) SEQUENCE DESCRIPTION: SEQ ID NO:14:

TCAGGAGAGT GTGGCTCCCA                    20

(2) INFORMATION FOR SEQ ID NO:15:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (xi) SEQUENCE DESCRIPTION: SEQ ID NO:15:

TGGAGCCTTC CTAACTGTGC                    20

(2) INFORMATION FOR SEQ ID NO:16:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (xi) SEQUENCE DESCRIPTION: SEQ ID NO:16:

AGACACAGGC TCACACATAC                    20

(2) INFORMATION FOR SEQ ID NO:17:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (  i i  ) MOLECULE TYPE: DNA (genomic)

(  i i i  ) HYPOTHETICAL: NO (  i v  ) ANTI-SENSE: NO (  v i  ) ORIGINAL SOURCE:
    ( A ) ORGANISM: Homo sapiens (  x i  ) SEQUENCE DESCRIPTION: SEQ ID NO:17:

GTCACCCATG CGCCCTCAGA 20

( 2 ) INFORMATION FOR SEQ ID NO:18:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear (  i i  ) MOLECULE TYPE: DNA (genomic)

(  i i i  ) HYPOTHETICAL: NO (  i v  ) ANTI-SENSE: NO (  v i  ) ORIGINAL SOURCE:
    ( A ) ORGANISM: Homo sapiens (  x i  ) SEQUENCE DESCRIPTION: SEQ ID NO:18:

GTGTTCTGGG GCCCTGGCCT 20

( 2 ) INFORMATION FOR SEQ ID NO:19:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear (  i i  ) MOLECULE TYPE: DNA (genomic)

(  i i i  ) HYPOTHETICAL: NO (  i v  ) ANTI-SENSE: NO (  v i  ) ORIGINAL SOURCE:
    ( A ) ORGANISM: Homo sapiens (  x i  ) SEQUENCE DESCRIPTION: SEQ ID NO:19:

ACTGCACTCC AGCCTCGGAG 20

( 2 ) INFORMATION FOR SEQ ID NO:20:

( i ) SEQUENCE CHARACTERISTICS:
    ( A ) LENGTH: 23 base pairs
    ( B ) TYPE: nucleic acid
    ( C ) STRANDEDNESS: single
    ( D ) TOPOLOGY: linear (  i i  ) MOLECULE TYPE: DNA (genomic)

(  i i i  ) HYPOTHETICAL: NO (  i v  ) ANTI-SENSE: NO (  v i  ) ORIGINAL SOURCE:
    ( A ) ORGANISM: Homo sapiens (  x i  ) SEQUENCE DESCRIPTION: SEQ ID NO:20:

ACAAAAGTCC TTTCTCCAGA GCA 23

( 2 ) INFORMATION FOR SEQ ID NO:21:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:21:

GGTCAGGATA GATCTCAGCT        20

( 2 ) INFORMATION FOR SEQ ID NO:22:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:22:

CACTTGCAAC TCCAGGAAGA CT        22